US 12,201,414 B2
Jan. 21, 2025

(12) United States Patent
Rowland et al.

(54) PRESSURE SENSING IMPLANT

(71) Applicant: ENDOTRONIX, INC., Lisle, IL (US)

(72) Inventors: Harry Rowland, Plainfield, IL (US);
Michael Nagy, Lombard, IL (US);
Nathan Plag, Naperville, IL (US);
Tyler Panian, Naperville, IL (US);
Suresh Sundaram, Dunlap, IL (US)

(73) Assignee: Endotronix, Inc., Naperville, IL (US)

( * ) Notice: Subject to any disclaimer, the term of this patent is extended or adjusted under 35 U.S.C. 154(b) by 656 days.

This patent is subject to a terminal disclaimer.

(21) Appl. No.: 16/851,225

(22) Filed: Apr. 17, 2020

(65) Prior Publication Data
US 2020/0260991 A1 Aug. 20, 2020

Related U.S. Application Data

(63) Continuation of application No. 15/213,712, filed on Jul. 19, 2016, now Pat. No. 10,638,955, which is a
(Continued)

(51) Int. Cl.
*A61B 5/07* (2006.01)
*A61B 5/00* (2006.01)
(Continued)

(52) U.S. Cl.
CPC ............ *A61B 5/076* (2013.01); *A61B 5/0031* (2013.01); *A61B 5/01* (2013.01); *A61B 5/0215* (2013.01);
(Continued)

(58) Field of Classification Search
None
See application file for complete search history.

(56) References Cited

U.S. PATENT DOCUMENTS

| 4,026,276 | A | 5/1977 | Chubbuck |
| 5,454,270 | A | 10/1995 | Brown et al. |
| 5,510,276 | A | 4/1996 | Diem et al. |
| 5,840,148 | A | 11/1998 | Campbell et al. |
| 6,278,379 | B1 * | 8/2001 | Allen ................. G01K 7/343 |
| | | | 340/447 |

(Continued)

FOREIGN PATENT DOCUMENTS

| CA | 2840645 A1 | 1/2013 |
| CN | 1701464 A | 11/2005 |

(Continued)

OTHER PUBLICATIONS

Patent Cooperation Treaty (PCT), International Search Report and Written Opinion for Application PCT/US12/44998, mailed Sep. 25, 2012, 9 pgs., International Searching Authority, US.

(Continued)

*Primary Examiner* — Michael R Bloch
(74) *Attorney, Agent, or Firm* — McDonald Hopkins LLC

(57) ABSTRACT

Disclosed is an implant and method of making an implant. The implant having a housing that defines a cavity. The housing includes a sensor comprising a base attached to a diaphragm wherein said base may be positioned within said cavity. The sensor may be a capacitive pressure sensor. The diaphragm may be connected to the housing to hermetically seal said housing. The sensor may include electrical contacts positioned on the diaphragm. The base may define a capacitive gap and a vent wherein the electrodes may be positioned within said capacitive gap such that at least a portion of the electrical contacts extend through the vent. The implant may include a coil in electric communication with the sensor, said coil may be positioned within said housing. A printed circuit board having at least one component may be attached to the floating base.

17 Claims, 16 Drawing Sheets

Related U.S. Application Data continuation-in-part of application No. 14/777,654, filed as application No. PCT/US2014/030661 on Mar. 17, 2014, now Pat. No. 10,226,218, said application No. 15/213,712 is a continuation-in-part of application No. 14/129,725, filed as application No. PCT/US2012/044998 on Jun. 29, 2012, now Pat. No. 9,867,552.

(60) Provisional application No. 61/786,793, filed on Mar. 15, 2013, provisional application No. 61/502,982, filed on Jun. 30, 2011.

(51) Int. Cl.
  *A61B 5/01* (2006.01)
  *A61B 5/0215* (2006.01)
  *A61B 5/03* (2006.01)
  *A61B 5/08* (2006.01)

(52) U.S. Cl.
  CPC .......... *A61B 5/02152* (2013.01); *A61B 5/036* (2013.01); *A61B 5/6876* (2013.01); *A61B 5/08* (2013.01); *A61B 5/6869* (2013.01); *A61B 2562/0247* (2013.01); *A61B 2562/168* (2013.01)

(56) References Cited

U.S. PATENT DOCUMENTS

| | | | |
|---|---|---|---|
| 6,939,299 B1 | 9/2005 | Petersen et al. | |
| 7,059,195 B1 | 6/2006 | Liu et al. | |
| 7,146,861 B1* | 12/2006 | Cook | G01L 9/008 |
| | | | 73/753 |
| 7,174,212 B1 | 2/2007 | Klehn et al. | |
| 7,191,013 B1 | 3/2007 | Miranda et al. | |
| 7,290,454 B2 | 11/2007 | Liu | |
| 7,353,711 B2 | 4/2008 | O'Dowd et al. | |
| 7,401,521 B2 | 7/2008 | Bellini et al. | |
| 7,432,723 B2 | 10/2008 | Ellis et al. | |
| 7,498,799 B2 | 3/2009 | Allen et al. | |
| 7,550,978 B2 | 6/2009 | Joy et al. | |
| 7,574,792 B2 | 8/2009 | O'Brien et al. | |
| 7,686,762 B1 | 3/2010 | Najafi et al. | |
| 7,763,487 B2 | 7/2010 | Villa et al. | |
| 7,932,732 B2 | 4/2011 | Ellis et al. | |
| 7,936,174 B2 | 5/2011 | Ellis et al. | |
| 7,973,540 B2 | 7/2011 | Kroh et al. | |
| 8,014,865 B2 | 9/2011 | Najafi et al. | |
| 8,104,358 B1 | 1/2012 | Jia et al. | |
| 8,111,150 B2 | 2/2012 | Miller et al. | |
| 8,118,748 B2 | 2/2012 | Schugt et al. | |
| 8,132,465 B1 | 3/2012 | Doelle et al. | |
| 8,154,389 B2 | 4/2012 | Rowland et al. | |
| 8,159,348 B2 | 4/2012 | Ellis | |
| 8,237,451 B2 | 8/2012 | Joy et al. | |
| 8,360,984 B2 | 1/2013 | Yadav et al. | |
| 8,373,559 B2 | 2/2013 | McCain | |
| 8,424,388 B2 | 4/2013 | Mattes et al. | |
| 8,493,187 B2 | 7/2013 | Rowland et al. | |
| 8,512,252 B2 | 8/2013 | Ludomirsky et al. | |
| 8,565,866 B2 | 10/2013 | Lomqvist et al. | |
| 8,665,086 B2 | 3/2014 | Miller et al. | |
| 8,669,770 B2 | 3/2014 | Cros | |
| 8,700,924 B2 | 4/2014 | Mian et al. | |
| 8,870,787 B2 | 10/2014 | Yadav et al. | |
| 8,901,775 B2 | 12/2014 | Armstrong et al. | |
| 9,265,428 B2 | 2/2016 | O'Brien et al. | |
| 9,305,456 B2 | 4/2016 | Rowland et al. | |
| 9,496,924 B2 | 11/2016 | Aber et al. | |
| 9,498,130 B2 | 11/2016 | Najafi et al. | |
| 9,712,894 B2 | 7/2017 | Lee et al. | |
| 9,839,732 B2 | 12/2017 | Armstrong et al. | |
| 10,022,054 B2 | 7/2018 | Najafi et al. | |
| 10,105,103 B2 | 10/2018 | Goldshtein et al. | |
| 10,143,388 B2 | 12/2018 | Cros et al. | |
| 10,205,488 B2 | 2/2019 | Hershko et al. | |
| 10,206,592 B2 | 2/2019 | Rowland et al. | |
| 10,307,067 B1 | 6/2019 | Xu | |
| 10,383,575 B2 | 8/2019 | Najafi et al. | |
| 10,478,067 B2 | 11/2019 | Najafi et al. | |
| 10,687,709 B2 | 6/2020 | Najafi et al. | |
| 10,687,716 B2 | 6/2020 | Goldshtein et al. | |
| 10,709,341 B2 | 7/2020 | White et al. | |
| 10,874,349 B2 | 12/2020 | Goldshtein et al. | |
| 10,874,479 B2 | 12/2020 | Forsell | |
| 11,154,207 B2 | 10/2021 | Campbell et al. | |
| 11,206,988 B2 | 12/2021 | Goldshtein et al. | |
| 2001/0018598 A1 | 8/2001 | Cruise et al. | |
| 2002/0111662 A1 | 8/2002 | Iaizzo et al. | |
| 2005/0273147 A1 | 12/2005 | Israel | |
| 2005/0288596 A1 | 12/2005 | Eigler et al. | |
| 2006/0109188 A1 | 5/2006 | Ikeda et al. | |
| 2006/0135963 A1 | 6/2006 | Kick et al. | |
| 2006/0137461 A1 | 6/2006 | Bellini et al. | |
| 2006/0177956 A1 | 8/2006 | O'Brien et al. | |
| 2006/0241354 A1 | 10/2006 | Allen | |
| 2006/0287602 A1* | 12/2006 | O'Brien | A61B 5/0031 |
| | | | 600/561 |
| 2007/0118038 A1 | 5/2007 | Bodecker et al. | |
| 2007/0163355 A1 | 7/2007 | Nassar et al. | |
| 2007/0199385 A1 | 8/2007 | O'Brien | |
| 2007/0208390 A1 | 9/2007 | Von Arx et al. | |
| 2007/0267708 A1 | 11/2007 | Courcimault | |
| 2008/0071339 A1 | 3/2008 | Stalker et al. | |
| 2008/0269573 A1 | 10/2008 | Najafi et al. | |
| 2008/0269829 A1 | 10/2008 | Li et al. | |
| 2009/0221885 A1 | 9/2009 | Hall et al. | |
| 2010/0100055 A1 | 4/2010 | Mustapha | |
| 2011/0046452 A1 | 2/2011 | Najafi et al. | |
| 2011/0063088 A1 | 3/2011 | Stevenson et al. | |
| 2011/0106120 A1 | 5/2011 | Haselby et al. | |
| 2011/0156178 A1 | 6/2011 | Zuniga-Ortiz et al. | |
| 2011/0224595 A1 | 9/2011 | Pedersen et al. | |
| 2013/0102858 A1 | 4/2013 | Hill et al. | |
| 2014/0028467 A1 | 1/2014 | Nagy et al. | |
| 2014/0155710 A1 | 6/2014 | Rowland et al. | |
| 2014/0306807 A1 | 10/2014 | Rowland et al. | |
| 2016/0029953 A1 | 2/2016 | Rowland | |
| 2016/0029956 A1 | 2/2016 | Rowland et al. | |
| 2020/0022601 A1 | 1/2020 | Rogers et al. | |
| 2020/0297218 A1 | 9/2020 | White et al. | |
| 2021/0068681 A1 | 3/2021 | Campbell et al. | |
| 2021/0275733 A1 | 9/2021 | Goldshtein et al. | |

FOREIGN PATENT DOCUMENTS

| | | |
|---|---|---|
| CN | 1826686 A | 8/2006 |
| CN | 101128957 A | 2/2008 |
| CN | 101278439 A | 10/2008 |
| CN | 101427923 A | 5/2009 |
| JP | 2000005136 A | 1/2000 |
| JP | 2002515278 A | 5/2002 |
| JP | 2003144417 A | 5/2003 |
| JP | 2005284511 A | 10/2005 |
| JP | 2006309582 A | 11/2006 |
| JP | 2007256287 A | 10/2007 |
| JP | 2008022935 A | 2/2008 |
| JP | 2010538254 A | 12/2010 |
| WO | 2009146089 A1 | 12/2009 |
| WO | 2012015955 A1 | 2/2012 |
| WO | 2013033506 | 3/2013 |
| WO | 2014170771 A1 | 10/2014 |
| WO | 2017115112 | 7/2017 |

OTHER PUBLICATIONS

Extended European Search Report for Application 12804636.4 PCT/US2012044998, dated Jan. 20, 2015, 6pgs., Eurpoean Patent Office, Germany.

Extended European Search Report for Application 14806873.7 PCT/US2014030661, dated May 20, 2016, 7 pp., European Patent Office, Germany.

(56) References Cited

OTHER PUBLICATIONS

Patent Cooperation Treaty (PCT), International Search Report and Written Opinion for Application PCT/US/14/30661, mailed Sep. 17, 2015, 8 pp., International Searching Authority, US.

International Search Report and Written Opinion of the International Searching Authority for PCT/US2017/042702 mailed Apr. 3, 2018, 14 pages.

Office Action in U.S. Appl. No. 16/727,230, mailed Apr. 25, 2024, 17 pages.

Examination Report in AU2022271366, mailed Dec. 5, 2023, 4 pages.

* cited by examiner

PRESSURE SENSING IMPLANT

CROSS-REFERENCE TO RELATED APPLICATIONS

This application is a continuation of U.S. patent application Ser. No. 15/213,712 entitled "PRESSURE SENSING IMPLANT" filed on Jul. 19, 2016 which is a continuation-in-part of U.S. patent application Ser. No. 14/777,654 entitled "PRESSURE SENSING IMPLANT" filed on Sep. 16, 2015 which is a national phase entry application that claims priority to International patent Application No. PCT/US2014/030661 filed Mar. 17, 2014 which claims priority to Provisional Patent Application No. 61/786,793 entitled "PRESSURE SENSING IMPLANT," filed on Mar. 15, 2013. U.S. patent application Ser. No. 15/213,712 is also a continuation-in-part of U.S. patent application Ser. No. 14/129,725 entitled "IMPLANTABLE SENSOR ENCLOSURE WITH THIN SIDEWALLS," filed on Feb. 21, 2014, which claims priority to International Patent Application No. PCT/US/2012/044998 entitled "IMPLANTABLE SENSOR ENCLOSURE WITH THIN SIDEWALLS," filed on Jun. 29, 2012 which claims priority to Provisional Patent Application No. 61/502,982 entitled "IMPLANTABLE SENSOR ENCLOSURE WITH THIN SIDEWALLS," filed on Jun. 30, 2011, each of which are hereby incorporated by reference in its entirety

FIELD OF INVENTION

This application relates to implant packages and more particularly to an implant for optimal wireless communication.

BACKGROUND

Implantable wireless sensors are useful in assisting diagnosis and treatment of many diseases. Examples of wireless sensor readers are disclosed in U.S. Pat. Nos. 8,154,389, and 8,493,187, each entitled Wireless Sensor Reader, which are incorporated by reference herein. Delivery systems for wireless sensors are disclosed in PCT Patent Application No. PCT/US2011/45583 entitled Pressure Sensor, Centering Anchor, Delivery System and Method, which is also incorporated by reference. In particular, there are many applications where measuring pressure from within a blood vessel deep in a patient's body is clinically important. For example, measuring the pressure in the heart's pulmonary artery is helpful in optimizing treatment of heart failure and pulmonary hypertension. In this type of application, a sensor may need to be implanted 10 to 20 cm beneath the surface of the skin.

Implantable wireless sensors that use radiofrequency (RF) energy for communication and power have been found to be particularly useful in medical applications. However, there are many tradeoffs and design constraints in designing such implantable sensors, such as size, cost and manufacturability.

A key challenge in successful commercialization of these implantable wireless sensors is the design tradeoff between implant size and the "link distance", which is the physical distance between the implant and the external device communicating with or providing energy to the implant. From a medical standpoint, it is desirable for an implant to be as small as possible to allow catheter based delivery from a small incision, implantation at a desired location, and a low risk of thrombosis following implant. However, from a wireless communication standpoint, the smaller the implant, the shorter the link distance. This distance limitation may be a function of the size of the antenna that can be realized for a given overall implant size. A larger antenna may be able to absorb more RF energy and transmit more RF energy than a smaller antenna. For example, in the case of wireless communication via inductive coupling, a typical implant antenna has the form of a coil of wire. The coil's "axis" is the line that extends normal to the plane of the windings, i.e. the axis is perpendicular to the wire's length. As the area encircled by the coil increases, the amount of magnetic flux that passes through it generally increases and more RF energy is delivered to/received from the implant. This increase in flux through the implant antenna can result in an increase in link distance. Thus to achieve maximum link distance for a given implant size, the implant antenna should be of maximal size.

While antenna size is important, other implant architectures may benefit from maximizing the size of other internal components. An implant containing an energy storage device such as a battery, for example, would enjoy longer battery lifetime with a larger battery. In another example, a drug-eluting implant could hold a larger quantity of the drug. Other examples will be apparent to those skilled in the art. Thus, it may be generally advantageous for an implant to have the largest possible internal volume, while maintaining the smallest possible external dimensions. This objective may be constrained by the implant's need for a strong, biocompatible, and hermetically sealed housing, to protect the internal volume from liquid ingress from the body environment.

Moreover, an optimal implantable sensor may be best designed to function with a specific device or reader device. Wireless transmitter and reader devices, such as the wireless reader of U.S. Pat. No. 9,305,456 and U.S. patent application Ser. No. 13/860,851 entitled "WIRELESS SENSOR READER," as well as U.S. patent application Ser. No. 14/041,738 entitled "WIRELESS SENSOR READER (SENSOR BANDWIDTH BASED ON AMBIENT CONDITION) which are hereby incorporated by reference herein in their entireties, may require a specific implantable sensor to provide optimal functionality of the reader/sensor system. An optimal implantable sensor for such systems may be configured to transduce pressure into an electrical resonant frequency. The sensor may be a passive sensor with no internal power source, such as a sensor having an LC resonant tank circuit. The sensor may minimize its total size while maximizing coil area, as described in PCT Patent No. PCT/US2012/044998 entitled "IMPLANTABLE SENSOR ENCLOSURE WITH THIN SIDEWALLS," which is hereby incorporated by reference herein in its entirety. The sensor may have a high RF Quality factor (Q), which is maximized by careful materials selection and device design. The sensor may be immune to temperature changes, including temperature changes during the manufacturing process and in transition between ambient conditions and in vivo. The sensor may have high sensitivity and good electrical isolation between electrical nodes and surrounding body fluids or tissue. The sensor may be highly stable over time, have good mechanical strength, incorporate biocompatible materials, and minimize use of ferritic materials. The sensor may be hermetically sealed to keep blood and other liquids from the body environment away from the internal electronics, possibly for the lifetime of the patient.

For an LC type wireless MEMS sensor, overcoming these challenges requires the design of a small sensor with high RF Quality factor (Q) at low operating frequencies (the human body attenuates wireless data signals, with generally more signal attenuation occurring at higher frequencies above 50 MHz). Additional challenges arise due to regulatory policies and licensed frequency bands for commercial use. With current technology, it is difficult to reliably fabricate an accurate ultra-miniature implantable wireless pressure sensor with high Q factor at low operating frequencies within a tightly controlled operating range.

To improve implantable wireless sensors, it is desirable to optimize various features of the sensor implant to ensure a high resonant quality factor may occur over the life of the implant.

SUMMARY OF THE INVENTION

This application relates to hermetically packaged wireless electronics and more particularly to an implantable sensor design and manufacturing approach to optimize manufacturability, size, longevity, RF characteristics, and overall performance.

In an embodiment, provided is an implant comprising a housing that defines a cavity. A sensor may be connected to the housing. The sensor may include a diaphragm and a floating base. The floating base may be attached to the diaphragm wherein the floating base may be positioned entirely within said cavity. The floating base may be attached only to said diaphragm. The sensor may be a capacitive pressure sensor. The diaphragm may be connected to the housing to form part of a hermetic seal about the cavity. The sensor may include electrical contacts such as electrodes positioned on said diaphragm. The floating base may defines a capacitive gap and a vent. The floating base and said diaphragm may defines the capacitive gap wherein an attachment between the floating base and the diaphragm includes a discontinuity that allows at least one electrical trace or electrode to connect outside the capacitive gap to at least one electrode positioned at least partially within the capacitive gap. The discontinuity may be a vent to allow the passage of fluid between the cavity and the capacitive gap. A coil may be in electric communication with said sensor and be positioned within said housing. The coil may include a coil axis wherein the coil axis may be substantially perpendicular to said diaphragm. A printed circuit board may be attached to the floating base and may include at least one electronic component. The electronic component may be a capacitor whose capacitance value may be adjusted by laser trimming, wherein said laser passes through said housing to perform the trimming. Implant parameters may be adjusted after hermetic sealing is complete by transmitting radiation through the housing to inside the cavity. The radiation may be one of laser, ultraviolet light, infrared light, focused light, and gamma radiation. The implant parameters that are adjusted may be performed by at least one of: ablating portions of electrodes on said sensor; ablating portions of a capacitor; ablating portions of tracks on a substrate; curing an adhesive; curing a coating; modifying an optically sensitive chemical; activating a thermally sensitive chemical; attaching items by welding; separating items by cutting; ablating a coating, film, or structure; and causing solder to reflow.

In another embodiment, provided is a method of making an implant. The method includes providing a housing that defines a cavity. A floating base may be attached to a diaphragm to form a sensor. The diaphragm may be attached to said housing such that said floating base is positioned within said cavity. A coil may be attached to said sensor. A bottom may be attached to said housing to form a hermetic seal about the cavity. A plurality of side walls may be welded together to provide said housing that defines said cavity. Alternatively, a continuous material may be machined to provide said housing that defines said cavity. The floating base may be made of a different material than said diaphragm. The diaphragm may be hermetically attached to said housing by a first laser weld about the perimeter of said cavity and a second laser weld about the perimeter of said cavity. The housing may include an integral base.

In another embodiment, provided is a method of making an implant. The method includes providing a housing formed from a continuous material that defines a cavity having an integral base with a top side and a bottom side. A diaphragm may be attached to said housing such that a capacitive gap is formed between said diaphragm and said top side of said integral base. A coil may be inserted into said cavity adjacent said bottom side of said integral base. A bottom wall may be attached to the housing adjacent the bottom side of said integral base to form a hermetic seal about said cavity. A wire bond cavity may be provided through said integral base. The coil may be electrically connected to said sensor through said integral base. Alternatively, the coil may be connected to said integral base with at least one "Through Substrate Via" (TSV).

In another embodiment, provided is an implant. The implant includes a housing that defines a cavity. A sensor may be connected to said housing. The sensor comprises a diaphragm having at least one diaphragm electrode and a base attached to the diaphragm. The base includes at least one base electrode wherein said base and diaphragm define a capacitive gap between the at least one diaphragm electrode and the at least one base electrode. The base may include a perimeter that is larger than a perimeter of the diaphragm such that the base attaches to the housing to define the cavity. The base may include at least one "Through Substrate Via" (TSV) to electrically connect the at least one of the base electrode and the diaphragm electrode to a component outside the capacitive gap. The base may be a floating base positioned within the cavity of said housing. The diaphragm may include a thick region and a thin region wherein the thin region is aligned with said capacitive gap between the at least one diaphragm electrode and the at least one base electrode. A coil may be in electric communication with said sensor, said coil may be positioned within said housing. A printed circuit board having at least one electronic component may be attached to the base and electrically attached to said coil. A distal anchor and a proximal anchor opposite the distal anchor may extend from the housing wherein the distal anchor and proximal anchor may form loops that extend from the implant. The anchors may be positionable in a fold down configuration and deployable from the fold down configuration to an open configuration. The proximal and distal anchors may be made of at least one of nitinol, platinum, stainless steel, polymer, and material which is biocompatible and extrudable. The sensor may be at least one of a pressure sensor, a temperature sensor, a gas sensor, and strain gauge. The housing may be attached to the diaphragm by at least one of laser welding, frit bonding, anodic bonding, fusion bonding, and eutectic bonding. The sensor may be electrically attached to the electronics wherein the electrical attachments are accomplished by at least one of wirebonding, soldering, ultrasonic bonding, wedge bonding, laser welding, and conductive adhesives. The implant may be an actuator and may include an energy storage unit within the cavity. The energy storage unit may be at least one of an electrochemical cell and a supercapacitor. An internal component may be provided within said cavity, the internal component may be a drug, a steroid, a battery, a stimulus electrode, a pacing circuitry, a flow sensor, or a chemical sensor. The implant may communicate wirelessly with an external unit. The implant may include a circuit having a resonant frequency that changes in response to a sensed parameter. The implant may include a circuit functional to perform at least one of modulation, demodulation, memory, ac/dc conversion, and signal conditioning. The housing and diaphragm may be made of a non conductive material. The PCB may include at least one chip-scale pressure sensor wherein the chip-scale pressure sensor communicates with the diaphragm through an internal pressure of said cavity.

In another embodiment, provided is an implant. The implant includes a housing that defines a cavity. A sensor may be connected to said housing. The sensor comprising a plate having at least two electrodes. A coil may be positioned inside said cavity wherein said coil may be attached to said electrodes forming a resonator and wherein said cavity is hermetically sealed. The implant may be configured to sense proximity, sense chemicals, or be configured for wireless communication.

BRIEF DESCRIPTION OF THE DRAWINGS

Embodiments of the present disclosure are described herein with reference to the drawings wherein.

DETAILED DESCRIPTION OF THE PREFERRED EMBODIMENTS

Reference will now be made in detail to embodiments of the invention, examples of which are illustrated in the accompanying drawings. It is to be understood that other embodiments may be utilized and structural and functional changes may be made without departing from the respective scope of the invention.

This application relates to an implant 10 and more particularly to an implantable sensor design and manufacturing approach to optimize manufacturability, size, longevity, RF characteristics, Q, and overall performance. To maximize RF link distance for a given implant size, the implant housing may be constructed to maximize antenna coil area, while still providing ample protection from the environment.

The implant 10 may include a housing 20 that may utilize thin membrane materials such as glass, quartz, sapphire, fused silica, alumina, titanium, diamond, or other materials, to increase the space available inside an implant package of a fixed outer size. Materials with low electrical conductivity may be used to prevent RF shielding of electromagnetic energy from the external unit, needed to power the implant, as well as the RF signal that is emitted by the implant. Electrically conductive or partially conductive housing materials may also be considered for systems in which power or signal transfer are at high frequencies, or implemented using other wireless energy transfer means such as ultrasonic, acoustic, et al.

Figure 1:
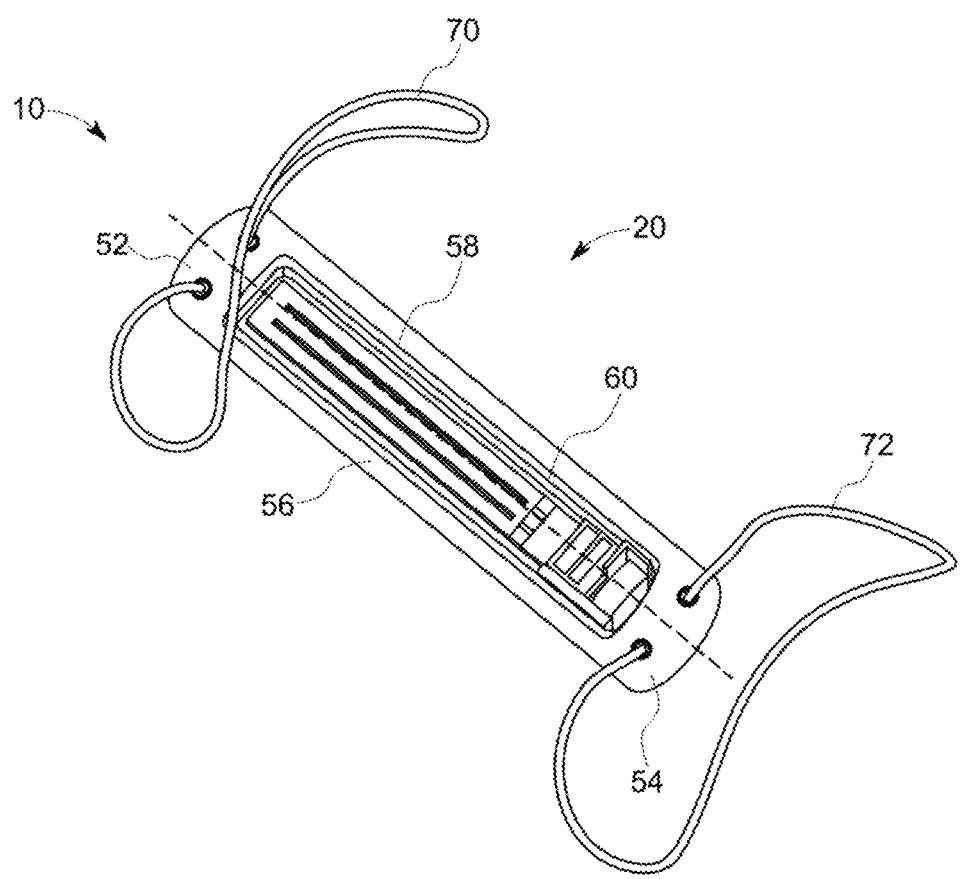
FIG. 1 is a perspective view of an embodiment for a wireless implant of the present disclosure.
Figure 3:
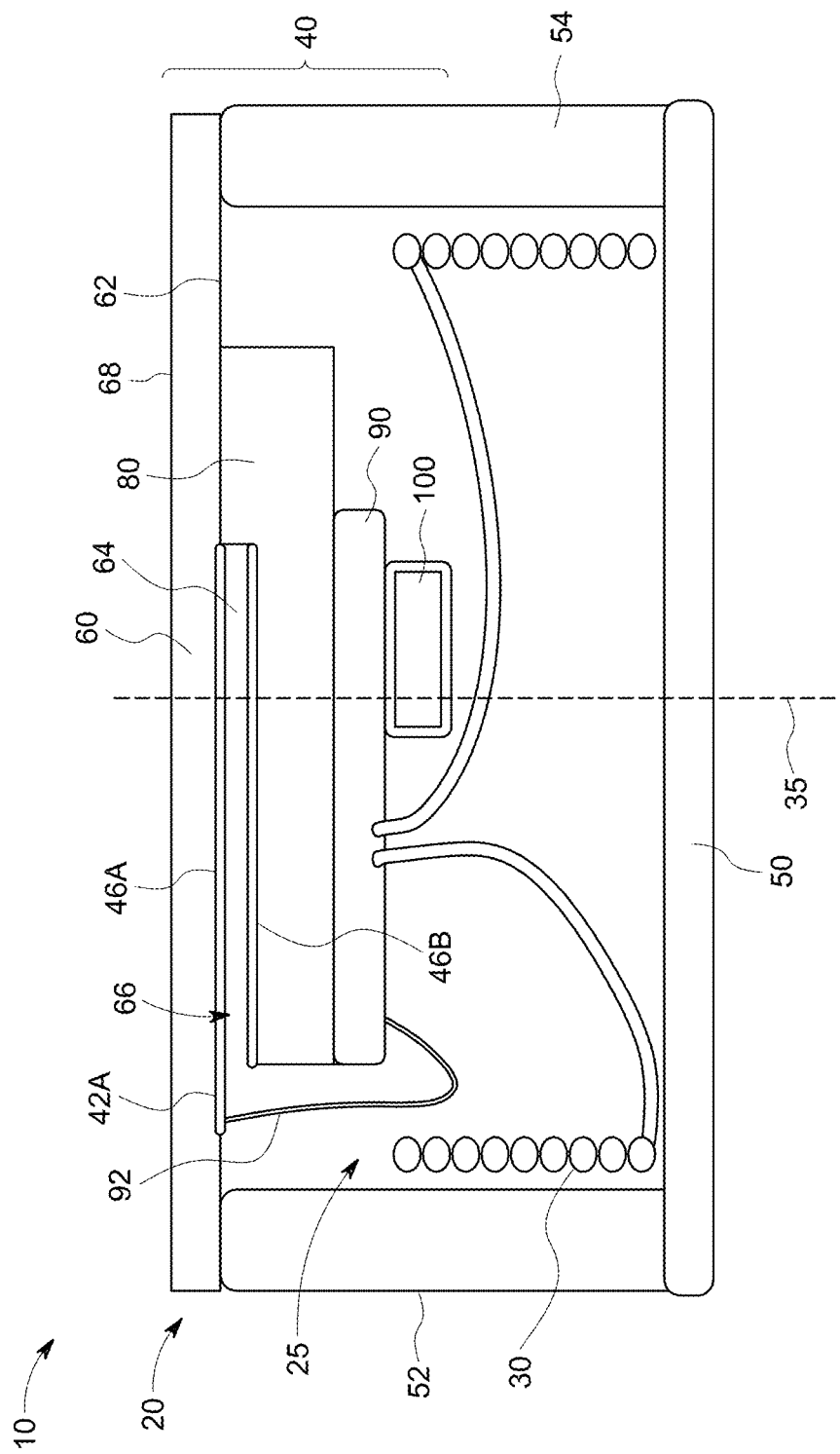
FIG. 3 is a schematic cross-sectional view of the implant of FIG. 1.
Figure 4:
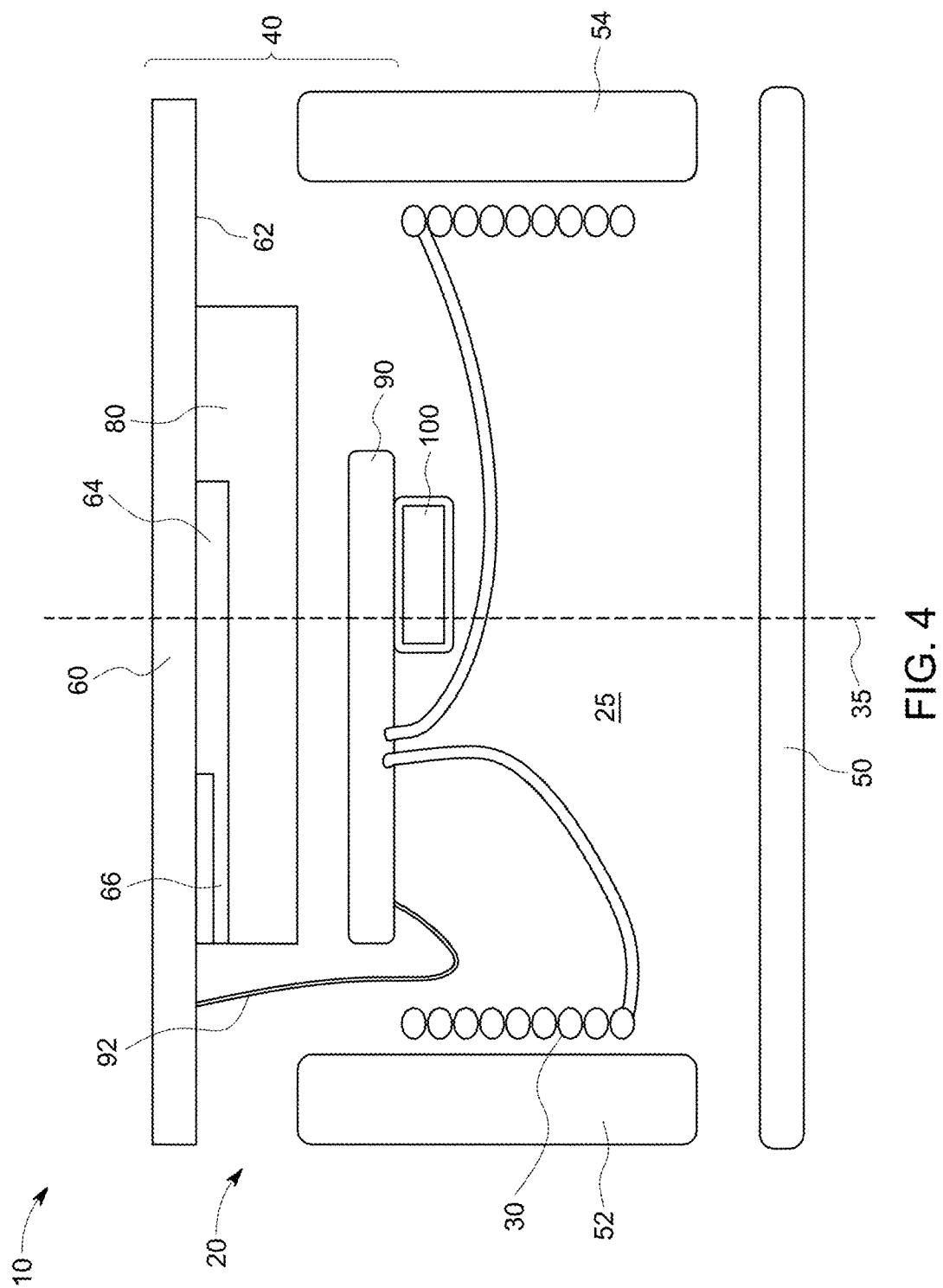
FIG. 4 is an exploded schematic cross sectional view of the implant of FIG. 1.

FIGS. 1, 3, and 4 illustrate a wireless implant housing 20 that maximizes coil area by its wall arrangement. The implant 10 may have an elongated, narrow, rectangular shape, although the housing may have various shapes and geometry. FIG. 1 illustrates an embodiment of the implant 10 in top perspective view and FIGS. 3 and 4 illustrate an embodiment of the implant 10 in cross section. The dimension of the housing 20 may be generally cuboid and may define a cavity 25 therein. The housing side walls may be of specific dimensions and proportions to each other. For example, the housing may have four side walls 52, 54, 56, and 58, a top wall 60 and a bottom wall 50. The housing 20 may be made of a hermetic, strong, and biocompatible material, such as ceramic. The housing 20 may be fabricated with processes, including micromachining, ultrasonic machining, wet etching, plasma etching, laser machining, conventional tool machining, injection molding, powder molding, or electrical discharge machining (EDM). The examples illustrate a cuboid housing, but other shapes and configurations may be used, such as cylindrical housings, prism-shaped housings, octagonally or hexagonally cross-sectioned housings, or the like. Additionally, any combination of walls 50, 52, 54, 56, 58, and 60 may be machined or molded as a single piece. For example, sidewalls 52, 54, 56, and 58 may be machined as a single piece and top wall 60 and bottom wall 50 may be created separately and then assembled to create the housing 20.

A distal anchor 70 and a proximal anchor 72 opposite the distal anchor may extend from the top side of the implant 10. The anchors may fixate the implant 10 in a desired position in the body of the patient and prevent it from moving. Notably, other anchor configurations and shapes may be implemented, including a different number of anchors (other than two); different locations of anchor attachment to the housing; anchors which attach to the housing at one point, or more than two points; anchors that extend under the housing, around it, or laterally to the sides; anchors with multiple loops or coils; and others. The anchors may be formed as loops which anchor the implant to body structures using spring force, or they may be designed to penetrate body tissues. The anchors may be made of nitinol, stainless steel, polymer, or any material which is biocompatible and extrudable. The anchors may be made of a combination of materials, such as nitinol with a platinum core. The anchors may be configured to fold down during the implantation procedure to allow easy ingress to the deployment location. The anchors may be configured to be tied down to a delivery system, such as a catheter, for minimally invasive ingress to the Implant deployment site. The anchors may be designed to deploy from their tied-down configuration to their open configuration when an operator actuates a control on the proximal end of the delivery system. The control may include release wires that are pulled from the proximal end either directly or with help from a mechanical handle. The anchors may be coated with a material to increase lubricity.

Figure 2:
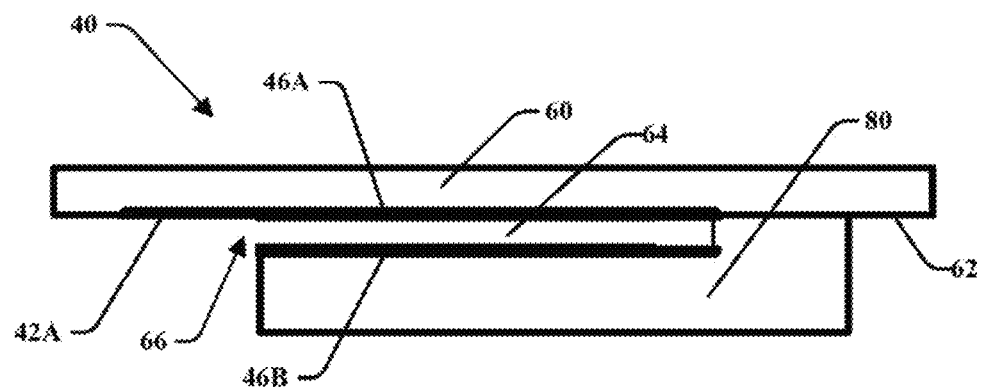
FIG. 2 is a schematic cross sectional view of the sensor component of the wireless implant of the present disclosure.

FIG. 2 illustrates the sensor 40 which may comprise one component of the implant 10. The sensor 40 may include the top wall 60 having electronic components placed thereon. The top wall 60 may be a diaphragm once bonded together with the remaining side walls. The sensor 40 may be Micro Electromechanical Systems (MEMS) type sensor. The sensor 40 may be a capacitive type sensor, formed by attaching a base 80 to the diaphragm 60. In one embodiment, a capacitive gap 64 may be positioned between the base 80 and the diaphragm 60. At least one of the base 80 and the diaphragm 60 may be etched to create the capacitive gap 64 at least partially between the base 80 and the diaphragm 60. Electrodes 46A, 46B may be patterned on either side of the capacitive gap 64 (See Figure. The electrode 46A may be placed on the diaphragm 60 and electrode 46B may be placed on the base 80. Electrode 46A may terminate to bond pads 42A, 42B which may be available to connect the electrode 46A to other components in the implant 10. The capacitive gap 64 may be vented to the outside of the sensor 40 by vent 66. The vent 66 may be a break in the bond or weld line between base 80 and diaphragm 60, which allows electrical traces or interconnect of the electrodes 46A to pass through and connect bond pads 42A, 42B. The attachment configuration between the base 80 and the diaphragm 60 may define a discontinuity that allows at least one electrical trace to connect outside said capacitive gap to at least one electrode positioned at least partially within the capacitive gap. The discontinuity may be the vent 66. The vent 66 may also allow the passage of fluid between the cavity 25 and the capacitive gap 64.

The underside 62 of the diaphragm 60 may be bonded to the base 80. Processes for this include laser welding, anodic bonding, fusion bonding, eutectic bonding, and glass frit bonding. Etching processes utilized for forming the sensor 40 include wet etching, dry etching, plasma etching, deep reactive ion etching (DRIE), laser machining, conventional machining, and ultrasonic machining. Possible electrode patterning processes include liftoff, sputtering, and laser machining. The sensor 40 may be a capacitive pressure sensor, wherein the diaphragm 60 may be designed to flex slightly and change the height of gap 64 when the top surface 68 and bottom surface 62 of sensor 40 are exposed to different pressures. The sensor 40 may be a force or strain sensor, wherein the diaphragm 60 may be designed to flex and change the gap 64 height when exposed to force or strain. The sensor 40 may be a temperature sensor, wherein the diaphragm 60 and base 80 may be made of different materials, designed to expand at different rates when exposed to temperature, and thus vary the gap 64. The sensor 40 may be an accelerometer, wherein the base 80 acts as a proof mass and changes the gap 64 height in response to acceleration or vibration. Electrodes 46A and 46B may include various discontinuities, such as slots or holes, in their patterning, to reduce losses due to eddy currents.

Minor variations to the basic design of the sensor 40 may be effected, to create other sensor types. Removing the base 80 may create a chemical sensor or a proximity sensor, wherein the top electrodes 46A may form an in-plane capacitor whose capacitance changes when the dielectric constant of the environment outside the top plate 60 changes, or when an object that affects capacitance (for example a metal object) gets sufficiently close to top plate 60. Patterning piezoresistive transducing elements onto diaphragm 60 may form a resistive type of sensor, which may transduce changes in diaphragm shape due to pressure, temperature, or strain into resistive changes. In such cases the base 80 may be eliminated; retaining the base 80 as a proof mass but eliminating electrode 46B may creates a sensor type that transduces acceleration into resistance.

The sensor 40 architectures may include a large overlapping area of the perimeter of the diaphragm 60 relative to the base 80. This feature may assist with the assembly of the implant 10. The base 80 and the diaphragm 60 may have various thicknesses and this disclosure is not limited. In one embodiment, the base 80 may be between 1 mm to 3 mm thick. The diaphragm 60 may be about 1 μm to 500 μm. As illustrated by FIG. 2, the "floating base" 80 includes a configuration having an area that substantially underlaps and hangs from the diaphragm 60. In an embodiment, the diaphragm may be about 150 μm thick. The diaphragm thickness may be selected to be structurally strong enough to form the top wall of the implant 10, and be stiff to minimize the amount of stiffness change caused by cell growth on the outer surface of the diaphragm. In an embodiment, the floating base 80 may be about 300 μm to 600 μm thick.

The diaphragm 60 and base 80 may be made from the same material or from different materials that are amenable to bonding and whose difference in thermal expansion coefficient may be such that the desired thermal properties may be obtained (either thermal stability or a known response to thermal changes). Materials for the diaphragm 60 and the base 80 may include glass, fused silica, quartz, sapphire, diamond, ceramic, silicon and its derivatives, germanium, SiGe and its derivatives.

The sensor 40 may be fabricated on wafer scale by a MEMS process. These components may be generally modular wherein a plurality of MEMs components and floating bases 80 may be manufactured along a single wafer.

FIG. 3 is a cross sectional sketch of an assembled implant 10 showing some of its constituent parts. In FIG. 3, the bottom wall 50, side walls 52, 54, 56, 58, and top wall 60 may be bonded together to form the housing 20 that defines the cavity 25. It will be appreciated that the walls may be hermetically bonded or sealed in any appropriate manner such as by welding, brazing, frit bonding, frit welding, eutectic bonding, anodic bonding, fusion bonding, or others. The side wall thicknesses of the housing walls are non-limited but may be thinner than the bottom wall 50 and the top wall 60. The side walls 52, 54, 56, and 58 may be attached to one another to form the cavity therein before the top wall 60 and bottom wall 50 to allow for various components to be placed therein. Alternatively, side walls 52, 54, 56, and 58 may be machined monolithically, in a generally continuous configuration, as a single four-sided unit, with an open top and bottom, and the top and bottom walls attached later. It may be etched or machined from a solid slab of material.

Figure 5:
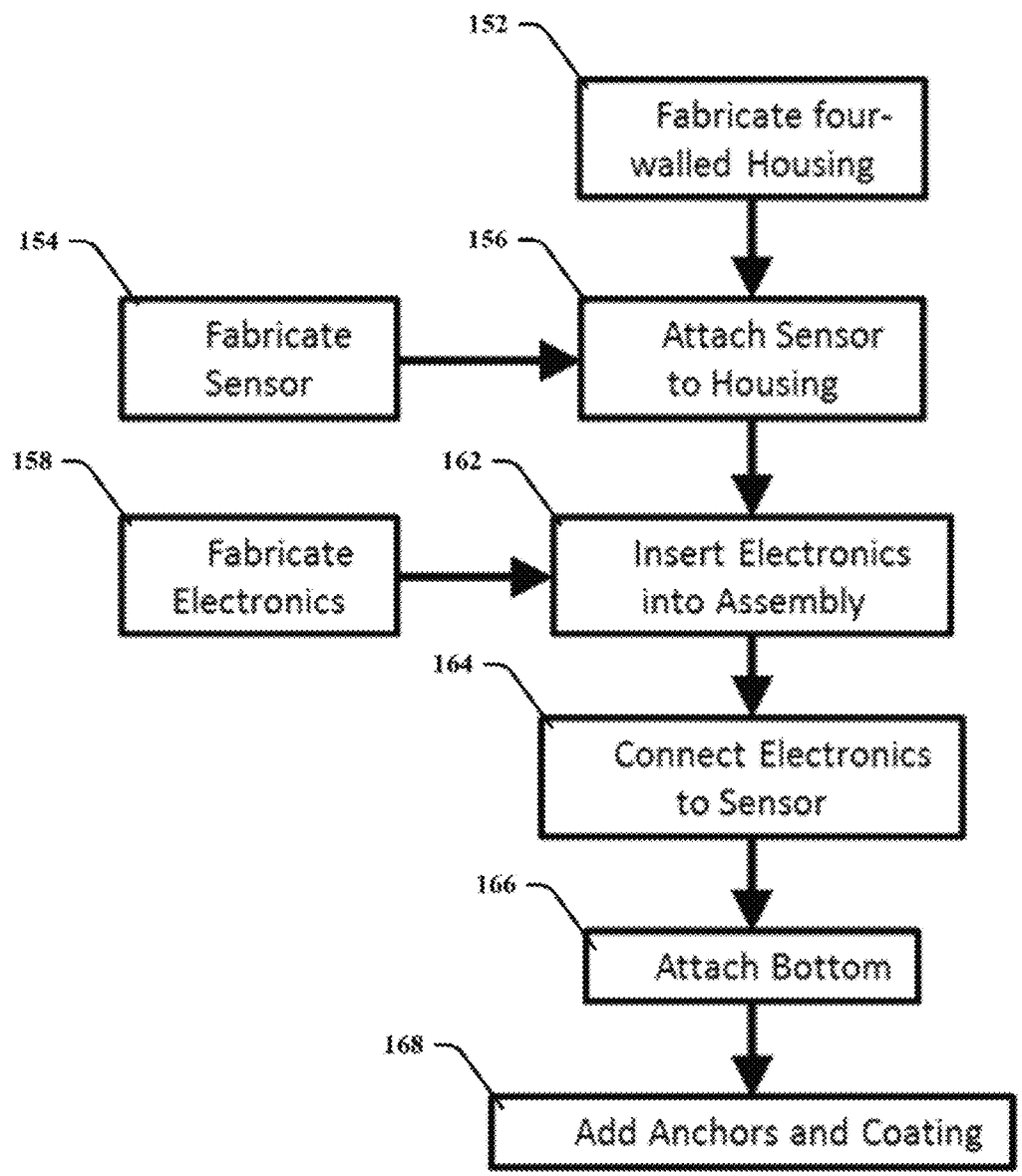
FIG. 5 is a flowchart illustrating a method of assembling an implant in accordance with the present disclosure.

FIG. 5 is a flowchart that illustrates an exemplary method for assembling the implant 10. FIG. 5 represents one possible process for a typical embodiment of the implant 10. Some steps may not be necessary, or can be carried out in a different sequence, or may include other steps. FIGS. 6-15 illustrate embodiments of assembling the sensor implant 10 that may be associated with the flowchart of FIG. 6.

In step 152, a housing may be formed having four sides 52, 54, 56, and 58. However, this disclosure is not limited as other shaped housings 20 are contemplated, such as cylindrical, triangular, pentagonal, hexagonal, or any shape, including asymmetrical configurations. The side walls, top wall, and bottom wall may be thinner than a design in which some or all of the housing is fabricated monolithically by a machining process. The walls of the housing 20 may be thinned by polishing, etching, or other methods and separately attached to one another to form the housing 20 and the cavity 25.

The sensor 40 may be fabricated as a standalone device, described by step 154. This may allow the sensor 40 to be screened by test or inspection before assembly into the implant 10. In-line screening tests and inspections at may actually occur along any point in the process to allow scrapping of unacceptable sensors 40 and prevent waste.

Figure 6:
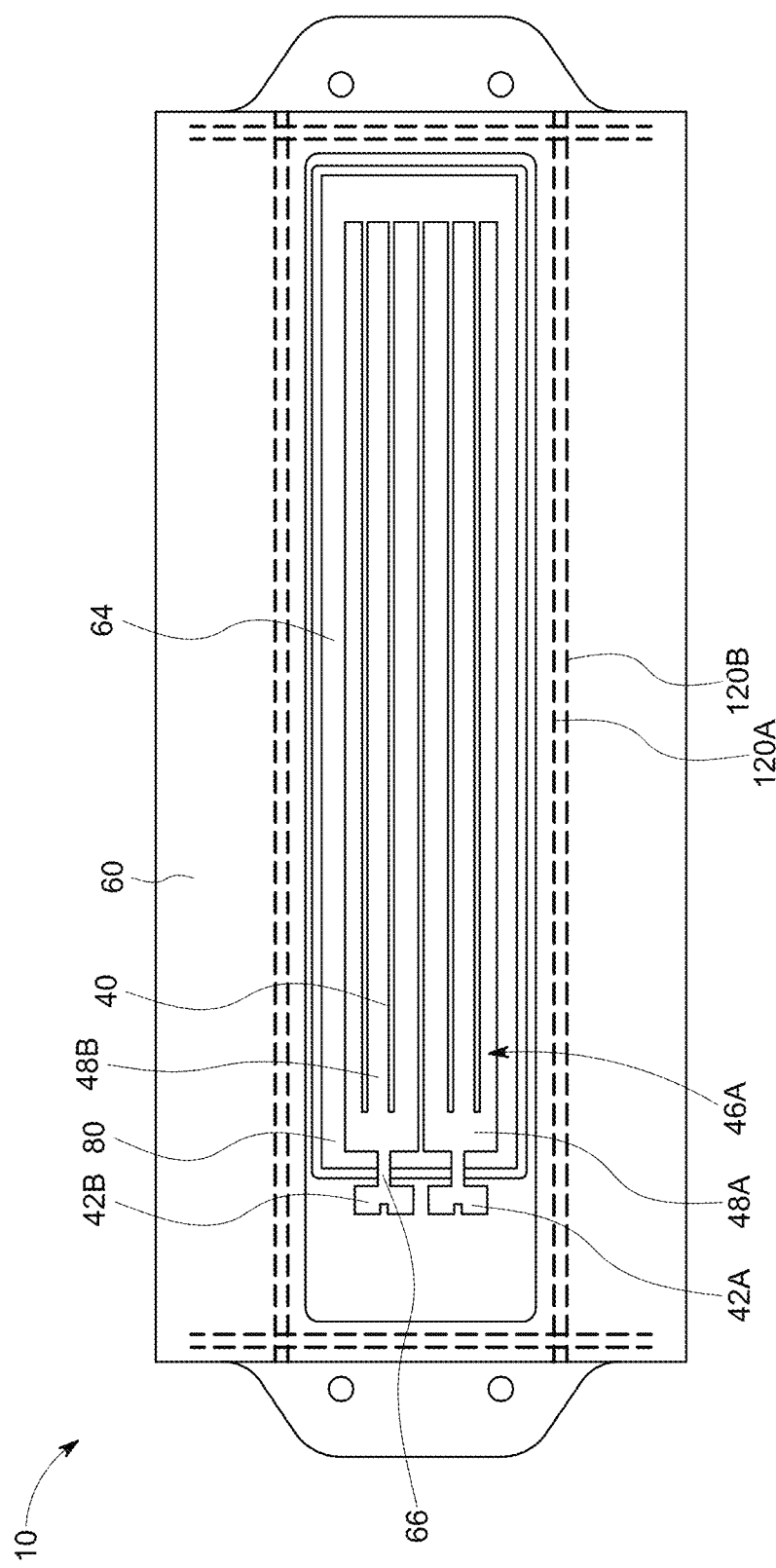
FIG. 6 is a top schematic view of a portion of a partially assembled implant of the present disclosure.

The sensor 40 may be attached to the housing 20 per step 156. FIGS. 3 and 4 illustrate the sensor 40 attaches to the sidewalls 52 and 54 of the housing 20, such that the floating base 80 resides inside the cavity 25. The diaphragm 60 may have a perimeter that overlaps the base 80 sufficiently to attach to the top surfaces of the side walls by one of the hermetic attachment methods available. Such means may include laser welding, frit bonding, anodic bonding, fusion bonding, or eutectic bonding, or other hermetic attachment method. The top surface 68 and the bottom surface 62 of the diaphragm 60 are shown as flat in the sketch, but these surfaces could have features etched or machined into them to facilitate fitting prior to attachment. Such features may include indentations, slots and ridges, holes and pegs, flanges, and the like. FIG. 6 illustrates a bonding technique that may be employed to attach the top wall 60, which is also the diaphragm 60, of the sensor 40, to the side walls of the implant 10. A first laser weld line 120A and a second laser weld line 120B may be employed to attach the side walls to the top wall. Each wall may include a double weld line about the perimeter of the side walls to ensure that the top wall 60 may be hermetically sealed to the side walls. FIG. 6 illustrates the first and second laser weld lines 120A, 120B between the top wall 60 and the side walls. Although two laser weld line are shown in this embodiment, other embodiments may use a single weld line, or any number of weld lines to affect the strength, stress, and hermetic properties of the weld.

Figure 7:
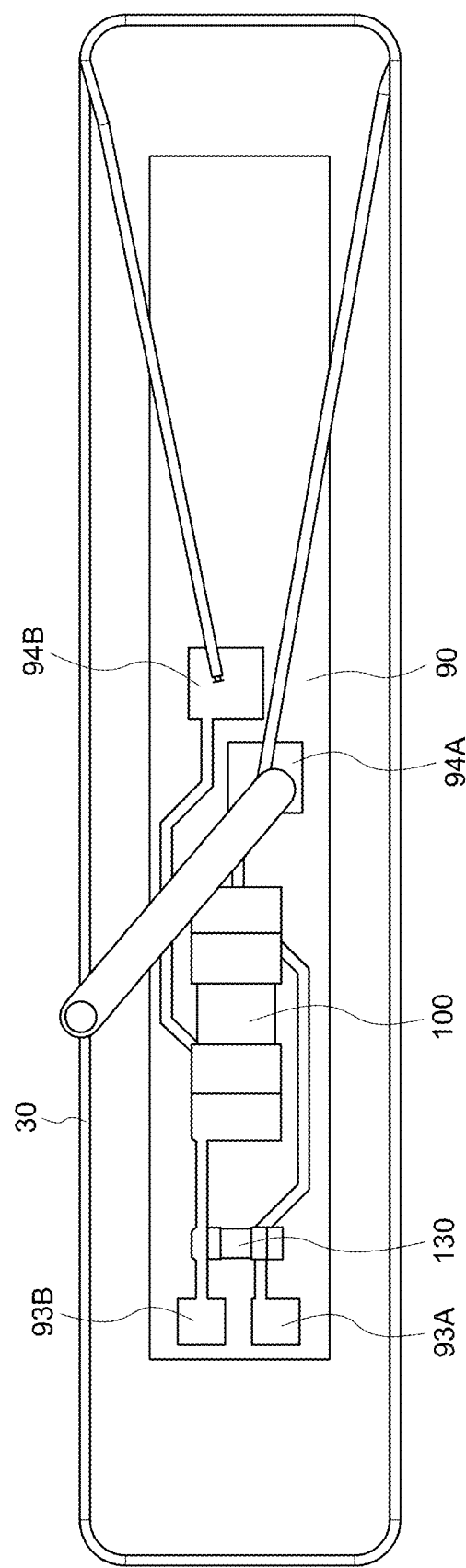
FIG. 7 is a top plan view of a coil and a printed circuit board for an embodiment of the implant.

The assembly or fabrication of electronics may occur in step 158 as illustrated by FIG. 7. The implant 10 includes an antenna coil 30 that may be placed into the cavity 25 of the housing 20. See FIG. 8. In one embodiment, the coil 30 is placed within the cavity via an opening in the bottom side of the housing 20 during assembly. Other electronic components, which may include one or more pressure sensors, may also be placed inside housing 20. The electronic components may be placed at least partially inside the region defined by the coil 30, or outside of this region. The electronic components may be positioned and attached along the inner surface 62 of the diaphragm 60. The coil 30 may be positioned such that it surrounds the floating base 80 and the electronic components partially or fully. The electronics and coil 30 may be assembled and interconnected electrically prior to insertion into the housing 20, or portions of the electronics and coil 30 may be inserted and then interconnected. See FIG. 7. By positioning the base 80 within the cavity 25 in a floating arrangement relative to the position of the coil 30, it may reduce the overall size of the implant 10. Additionally, during assembly, this configuration allows for accessibility to the electrodes without through vias or holes.

In the case where implant 10 contains a pressure sensor 40, the internal electronic components may include one or more pressure sensors such as MEMS pressure sensor components and the top wall 60 may be a diaphragm such as a flexible membrane. The top wall 60 and electrodes 46A, 46B may communicate pressure by slight vibrations. Also, a gas, a fluid, or a gel may fill the cavity 25 formed by the housing 20. In another embodiment, the bottom wall 50 may also be a diaphragm such as a flexible membrane which may include additional electrical components that may also be part of a sensing electronic circuit (not shown). In either embodiment, pressure measurements may be transduced directly into an electronic signal of a sensing circuit or component.

In other embodiments, sensor 40 may be a different type of sensor 40, comprising only a single plate with at least two-coplanar electrodes and no base. Such a sensor can sense changes in the capacitance between the co-planar electrodes due to metal objects outside of the hermetic enclosure, or changes in capacitance due to chemical changes outside the enclosure. Coating the outside of the plate with a chemical that reacts with the environment in a desired way, to change capacitance can enhance this configuration.

The electronics may comprise one or more components 100, 130. The components 100, 130 may serve as a trim element, to adjust the resonant frequency of the overall implant to a desired value for operation. The components 100, 130 may be capacitive elements, inductive elements, or other electrical components. The components 100, 130 may be resistive elements configured to adjust the Q factor of the implant 10. They may be temperature sensitive elements configured to compensate for changes in temperature. They may be active circuits or integrated circuits. They may include modulating circuits, analog to digital conversion circuits, rectifiers, or other circuits. Additionally, a printed circuit board (PCB) 90 may be used to provide a mounting surface and electrical interconnection of the various electronic components 100, 130. The PCB 90 may be positioned on the floating base 80. The PCB 90 may include electrical traces thereon to allow for electrical coupling to the coil 30, electric components 100, 130, and may be electrically coupled to the electrodes 46A, 46B on the diaphragm 60 via wirebonds 92. The PCB 90 may be any substrate that provides means for electrical connectivity between components. The PCB 90 substrate material may be plastic such as FR4, ceramic, glass, Rogers board, flex PCB, polyimide, silicon, quartz, paper, or other materials useful for this purpose. This allows for a variety of patterns wherein the connection between the coil 30, the sensor 40, and any other electronic components such as trim elements, may be accomplished through the PCB 90. As illustrated by FIG. 7, the coil 30 may be electrically connected to the PCB 90. The coil 30 may be soldered to electric traces 94A, 94B positioned along the PCB 90. Other electric connections, such as wedge bonding, ultrasonic welding, laser welding, or conductive adhesive, may also be utilized. The PCB 90 may be positioned within the perimeter of the coil 30. In one embodiment, the PCB 90 may include electrical components such as a first capacitor 100 and a second capacitor 130 in electrical communication with the traces 94A, 94B and the coil 30.

The coil 30 may be wound about center axis 35 as shown in FIG. 3. The center axis may be generally parallel with the side walls 52, 54, 56, and 58 and may be generally perpendicular to the top wall 60 and the bottom wall 50. By orienting the top and bottom walls 60, 50 such that they are generally perpendicular to the center axis 35 of coil 30, this allows for more efficient assembly and use of space. In this way, the implant housing 20 may achieve the maximum cavity 25 area within the width constraint imposed on the short dimension. It will be appreciated that the coil axis 35 refers to the central axis of a generally spirally wound coil 30, as shown in FIG. 3. The spirally wound coil 30 may be any appropriate shape, such as circular, rectangular, or any other shape. The coil 30 may encircle the largest possible area within the cavity 25 of the implant 10. The larger the area of the coil may provide a larger coupling coefficient for communication with an antenna of an external element. The external element, such as a reader, may provide power to the implant 10 and receive power or signals from the coil 30. This inductive coupling between the coil 30 and the reader is disclosed by U.S. Pat. No. 9,305,456, incorporated by reference herein. A larger coupling coefficient may provide more power to the implant 10 during energization, and may provide a stronger signal to the external reader unit when the implant 10 is transmitting or ringing back at a resonant frequency.

FIG. 3 shows the coil 30 extending vertically up to alignment with the PCB 90. In another embodiment, the base 80 may be sized such that the coil 30 can wrap around the base 80 and PCB 90, extending upwards in height until it spans the distance between the bottom surface 62 of the diaphragm 60 and the bottom wall 50 of the implant 10. Increased coil 30 space allows for additional coil height which allows for additional coil turns. Coil 30 size may effect coil inductance, Q factor, coupling coefficient, and implant sensitivity. Coil 30 height can also be increased by increasing the thickness of the coil wire, which may also increase Q factor for the implant 10.

The inner surface of the cavity 25 may be shaped to correspond to the shape of the coil 30 such that the coil 30 frictionally abuts against the inner surface of the side walls for a snug fit within the housing 20. This configuration allows the coil 30 to surround the floating base 80 and may allow for a taller coil dimension within the cavity 25. Alternatively, the side walls 52, 54, 56, 58 may include an annular ridge or protrusion 96 (FIG. 9) formed about at least a portion along the perimeter of the cavity 25 such that the coil 30 may be slightly deformed during assembly to overcome the annular ridge 96 to be retained within the cavity 25. The annular ridge 96 may extend inwardly from the side walls 56, and 58. In yet another embodiment, coil 30 may be wound about a bobbin, made of plastic, ceramic, glass or a ferritic material. The bobbin may provide structure to the coil 30 to prevent false readings due to coil motion, to facilitate handling during assembly, or to change the coil's electrical properties.

Figure 8:
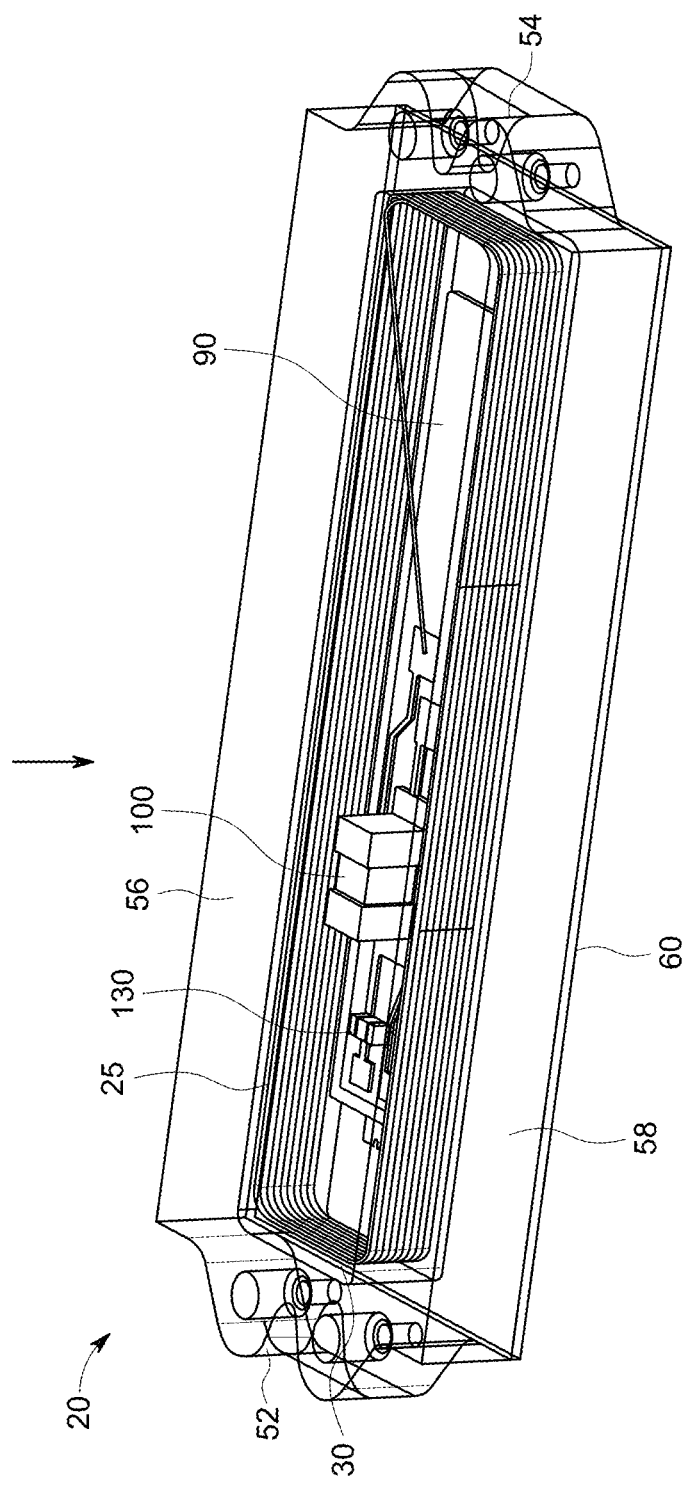
FIG. 8 is a perspective schematic view of the coil and printed circuit board being inserted within a housing of the implant.
Figure 9:
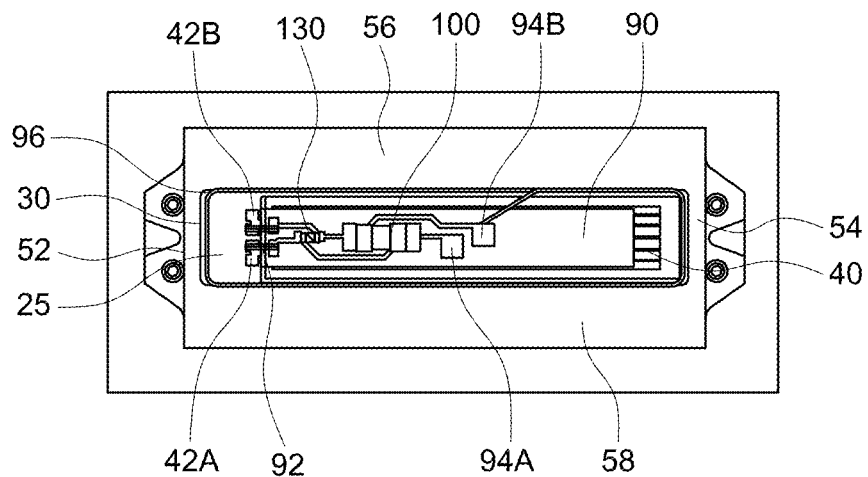
FIG. 9 is a bottom view of a partially assembled implant without a bottom wall.

FIG. 8 illustrates an embodiment of the housing 20 during assembly step 162 of FIG. 5. Here the coil 30 and PCB 90 may be placed within the cavity 25 through the bottom opening. The PCB 90 may be attached to the floating base 80 of the sensor 40 and the coil 30 may be inserted within the side walls 52, 54, 56, and 58. The PCB 90 may be glued or otherwise attached to the floating base 80 on the underside of the top wall 60. Referring to FIG. 9, which is a view into the cavity 25 through the bottom of the partially assembled implant 10, the bondpads 42A, 42B of the sensor 40 may be electrically attached to the PCB 90 by wirebonds 92. The bondpads 42A, 42B may be laterally opposed such that the wirebonds 92 are attached to electrical traces 94A and 94B in electrical communication with the coil 30, first capacitor 100, and second capacitor 130, as shown in FIG. 9. In one embodiment, two wirebonds 92 may be made from each bondpad 42A, 42B to bondpads 93A, 93B at the end of each electrical trace 94A, 94B. Further, in one embodiment, the second capacitor 130 may be a capacitive temperature sensor provided on the PCB 90. This second capacitor 130 may function to normalize capacitance related to temperature. As temperature increases, the capacitance may increase, which may counteract the effect of gas expansion, which may cause the capacitance of the sensor 40 to decrease. The second capacitor 130 may help reduce sensitivity to temperature changes.

In yet another embodiment, the PCB 90 may be eliminated as a separate component, and the interconnect pattern and pads may be deposited directly onto base 80. In yet another embodiment, the walls 52, 54, 56, or 58 of the housing 20 may have a flange that extends inwardly to support the PCB 90. This arrangement may serve to reduce stress on the base 80.

Step 164 of FIG. 5 describes connecting the sensor 40 to the assembly that includes the electronics and the coil 30. It should be understood that the steps of FIG. 5 may be performed in a different sequence than that shown, depending on details of the implant 10 design, as well as process capabilities and priorities. In FIGS. 2, 3, and 6, the electrodes 46A, 46B of the sensor 40 are arranged in a series pattern otherwise referred to herein as the "serial capacitor" embodiment. In this embodiment, the top electrode 46A may include a plurality of electrodes 48A and 48B as illustrated by FIG. 6. The bottom electrode 46B may be a single electrode. This electrode arrangement creates a first capacitor 46B-48A that is in series with a second capacitor 46B-48B. Electrodes 48A and 48B include bondpads 42A and 42B, respectively (as illustrated by FIG. 6), and the bondpads 42A, 42B are accessible to make the electrical connection with the wirebonds 92 as illustrated by FIG. 9.

In one embodiment, the series capacitance architecture may have a decreased overall capacitance compared to a parallel capacitance architecture. However, this configuration allows bondpads 42A and 42B to be accessible for electrical connection. In one embodiment, the electrodes 48A, 48B extend from the gap 64 through the vent 66 of the floating base 80 to bondpads 42A and 42B. The electrodes 48A, 48B may be placed near one another such that the wirebonds 92 are attached along only one side of the diaphragm 60. This allows for a shorter interconnect which may provide for an improved manufacturing step and improved Q factor. The connection of the sensor 40 to the electronics may be accomplished by conventional wirebonding, soldering, ultrasonic bonding, wedge bonding, laser welding, conductive adhesives, or other means known to those in the art.

Figure 10:
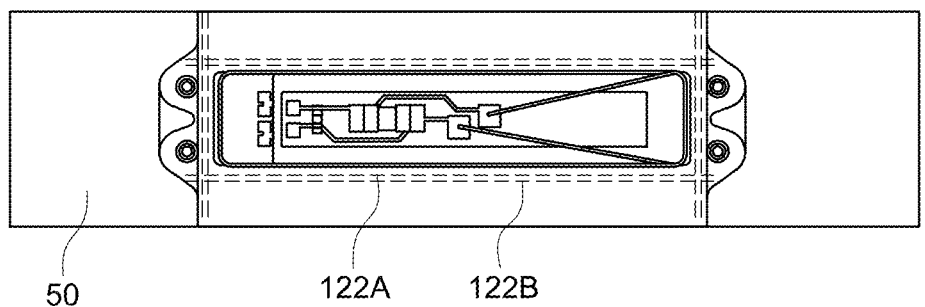
FIG. 10 is a bottom view of the implant during assembly, with a bottom side attached to the housing via laser welds.

In step 166 of FIG. 5, the bottom 50 may be attached to the housing 20, completing the hermetic enclosure. The bottom wall 50 may cover the cavity 25 and abut against the bottom portion of side walls 52, 54, 56, and 58 as illustrated by FIG. 10. The bottom wall 50 may be attached to the side walls with a first laser weld line 122A and a second laser weld line 122B. Each wall may include a double weld line about the perimeter of the side walls to ensure that the bottom wall 50 may be hermetically sealed to the side walls, and to increase weld strength. Other embodiments may use single weld lines, partial weld lines, or multiple weld lines.

Figure 11:
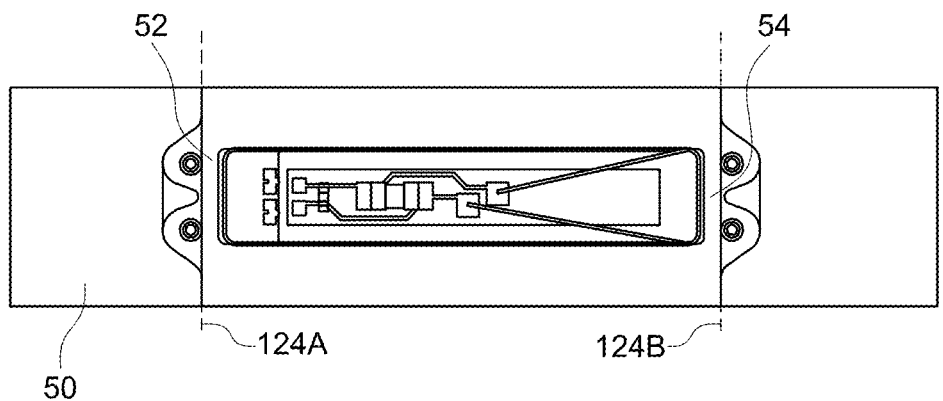
FIG. 11 is a bottom view of the implant during assembly with trim lines along the bottom side.
Figure 12:
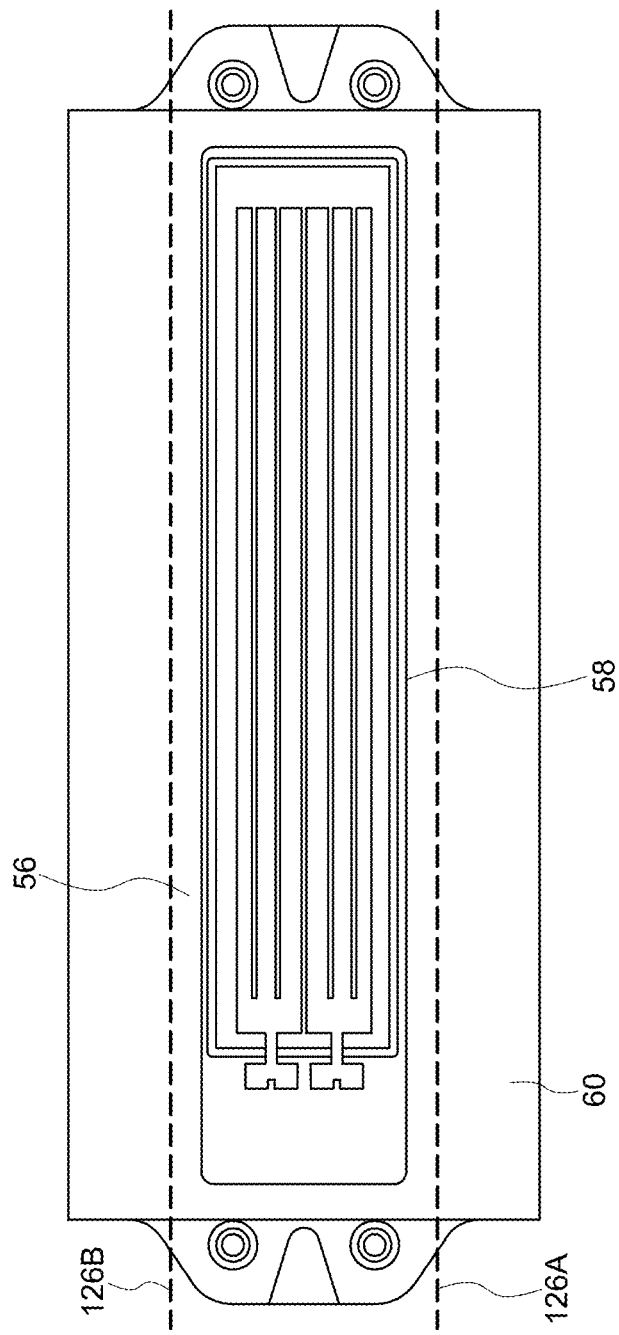
FIG. 12 is a top view of the implant during assembly with trim lines along the top side.
Figure 13:
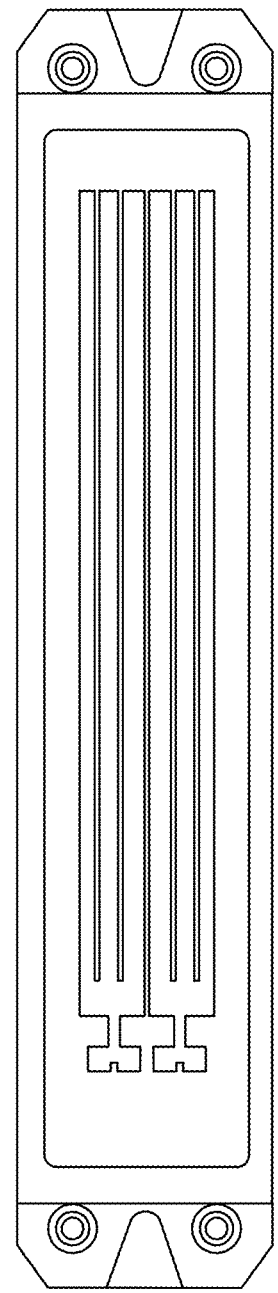
FIG. 13 is a top view of the implant during assembly.

Further, scribe lines may be applied to the bottom wall 50. FIG. 11 illustrates first and second scribe lines 124A, 124B on the bottom wall 50 in alignment with an outer perimeter of the side walls 52 and 54. FIG. 12 illustrates second and third scribe lines 126A, 126B applied along the top wall 60 in alignment with an outer perimeter of the side walls 56 and 58. The scribe lines allow excess pieces of the bottom wall 50 to be removed from the housing 20 to form the sensor implant 10 having a compact shape as illustrated by FIG. 13.

The bottom wall 50 may be fabricated as a thin film with a thickness between about 100-200 µm, in one embodiment. The bottom wall 50 may be made from any material that can be attached to the housing 20. Possible materials include, but are not limited to glass, quartz, sapphire, fused silica, alumina, titanium, and diamond.

Prior to step 166, in some embodiments, additional items or materials may be placed within the cavity 25 to enhance implant 10 performance. Step 166 may take place in an air environment, or in another gas selected for its properties. Examples may include dry air or dry inert gas to reduce humidity inside the implant 10. The bottom 50 may be attached in a vacuum, or a pressure other than ambient pressure. If the implant 10 is being used to sense pressure, a non-ambient internal pressure may be used to bias the implant towards a certain pressure, or to change the effects of internal gas expansion due to temperature change. The cavity 25 may be filled with a liquid or gel, used for example in a design where chip-scale pressure sensors reside on PCB 90, and the liquid or gel transfers pressure from the diaphragm 60 to the chip scale pressure sensors. The cavity 25 may contain fluoroscopic ink, paint, contrast die, or other material or hardware designed to make the implant 10 visible under fluoroscopy. The cavity 25 may contain a getter or desiccant material to remove moisture, water or other undesired materials from other areas within cavity 25. Desiccant may assist with controlling humidity or moisture within the cavity as moisture may cause the electrical components to drift or otherwise provide errors. Additionally, the desiccant may be adapted to change color when a change in humidity is detected and viewed through the transparent top and bottom walls. The cavity 25 may contain ferritic or other material to alter the properties of the coil 30 or other components. The cavity 25 may contain a gel, insert, or other material to alter the dielectric constant or other properties of the internal implant components. The cavity 25 may contain a bladder, whose stiffness is significantly lower than that of the pressure sensitive diaphragm 60, which may compress more readily than diaphragm 60 when gas pressure inside the cavity 25 increases due to temperature change.

Figure 15:
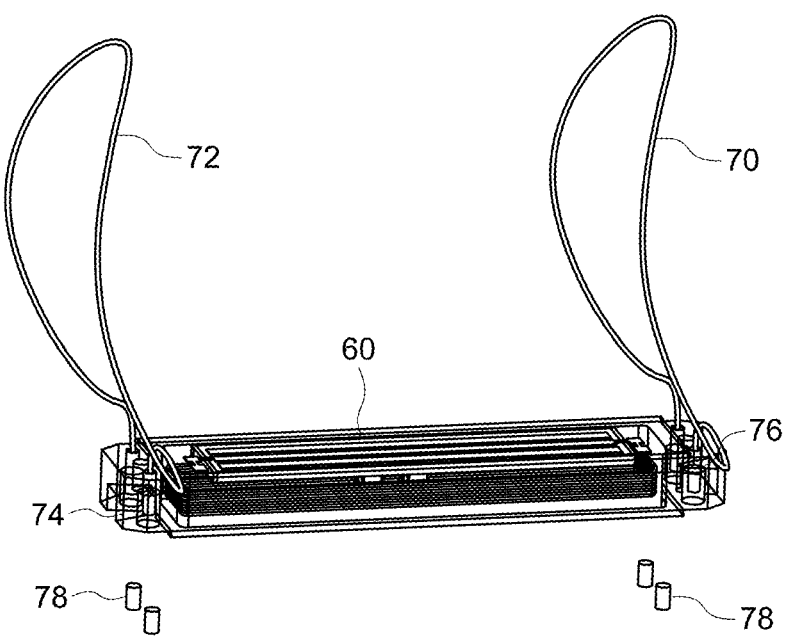
FIG. 15 is a perspective view of the implant during assembly with anchors and marker bands attached to the ends of the implant.

After the bottom 50 has been attached, the assembly of the implant 10 may, in some embodiments, proceed to step 168 of FIG. 5. In this step, anchors 70 and 72 may be attached, and the body of the implant 10 may be coated with a material. A variety of anchor sizes, shapes, and attachment methods are possible. FIG. 15 illustrates the housing 20 with apertures 74, 76 that extend through side walls 52, 54 to receive the anchors 70, 72. The distal anchor 70 and the proximal anchor 72 may be inserted into the apertures 74, 76. Marker bands 78 may be attached to the ends of the anchors 70, 72 within the apertures 74, 76 to retain the anchors to the housing 20 and allow the anchors to extend from the top side 68 of the implant 10. In one embodiment, the marker bands 78 may be made from radiopaque ink that may show up in various medical scans to identify the orientation of the implant 10 as it is positioned within the patient. The anchors may extend from the same side as the diaphragm 60.

Once the anchors have been attached to the housing 20, a coating may be applied to portions of the outer surface of the implant 10. In one embodiment, the coating may be a silicone dip coating or dispersion coating. The thickness of the coating may be between about 25 µm to about 100 µm. A variety of other coatings may be considered, including parylene or other polymers. Coatings may be applied for their hydrophilic or hydrophobic properties, or to provide lubricity, mechanical strength, or fluoroscopic visibility. Coatings may be applied by dipping, spraying, vapor deposition, or other means in the art.

The implant 10 may meet the complex requirements of medical implants: (i) small cross-sectional area, (ii) non-metal housing, (iii) hermetic sealing, (iv) biocompatibility, and (v) maximum internal volume for a given external volume.

Figure 14:
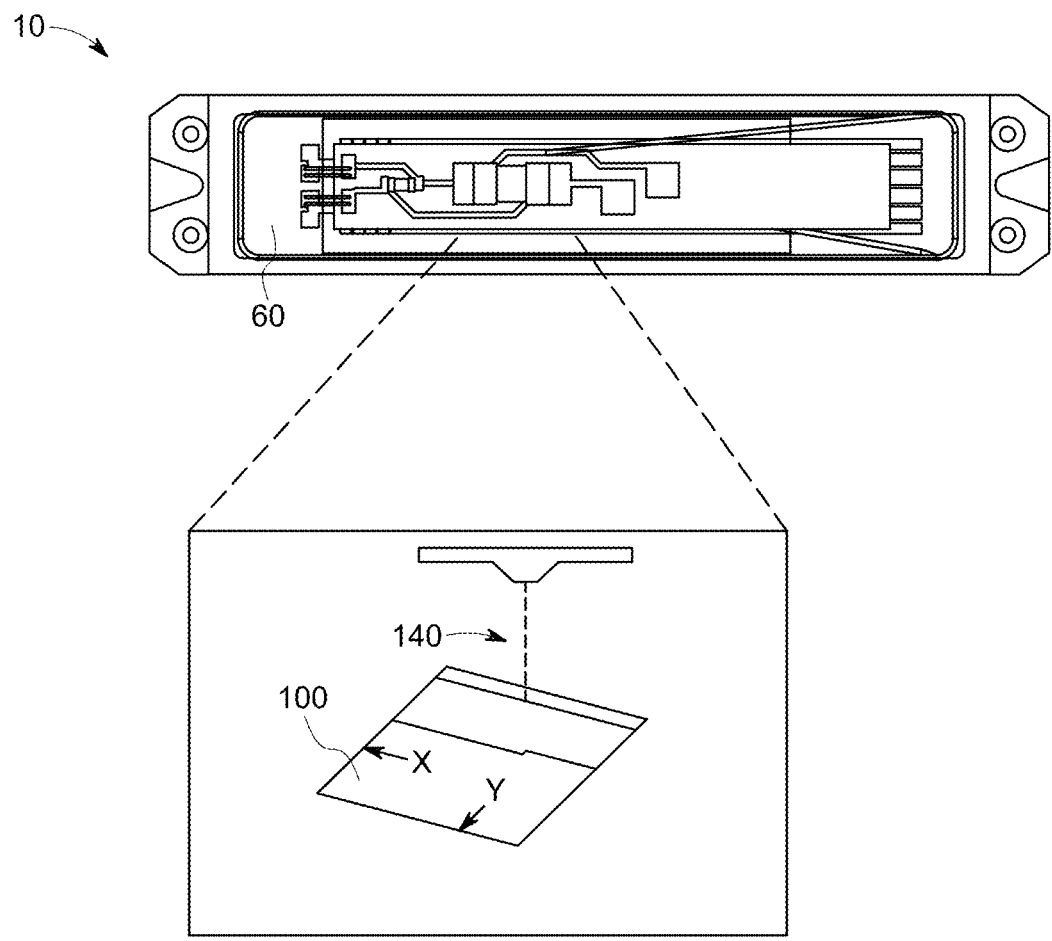
FIG. 14 is a bottom view of the implant during assembly with an enlarged window that illustrates a laser-trimmable capacitor.

Any of the side walls 53, 54, 56, 58, bottom wall 50, and diaphragm 60 may be generally transparent to allow one to view the components within the cavity 25 from outside the housing 20. After the implant 10 has been assembled, it may be possible to adjust the functionality of the implant 10 to ensure that it may be compatible with a particular sensor reader. FIG. 14 illustrates that a laser beam 140 may be applied to the electric components through the top wall 60 to adjust the components in a desired manner. In particular, the first capacitor 100 may include a surface that may be affected by the laser beam. The capacitor 100 may be trimmable such that the laser may ablate part of an electrode on the surface of the first capacitor 100 to decrease the capacitance and change a property of the implant 10, such as the resonant frequency. In one embodiment, the first capacitor 100 is adjusted to allow the implant sensor to transmit a signal in response to an excitation pulse at a desired frequency range. In one embodiment, that frequency range is between 5 MHz to 30 MHz, and more particularly between 10 MHz to 20 MHz, or between 12 MHz to 15 MHz, and preferably between 13.4 MHz to 13.6 MHz. Further, additional electronic adjustments may be made after assembly due to the transparent housing. Tracks on PCB 90 may be ablated by laser to add, remove, or reconfigure components within the circuitry. Notably, certain adhesives may be cured by the application of UV energy. MEMS electrodes may be trimmable, and resistors, ship inductors or other electrical components may be trimmable by the application of a laser beam through the housing. Sterilization of the components within the implant 10 may be accomplished through irradiation by gamma particles or other means. Other chemical or physical processes that can be affected or catalyzed by the application of light energy can also be carried out. An advantage to transparent or partially transparent sidewalls is that these adjustment steps may be carried out after the implant 10 has been hermetically sealed. These adjustments may be done in response to final measurements of the implant 10, and not rendered invalid or inaccurate by later process steps.

Figure 28:
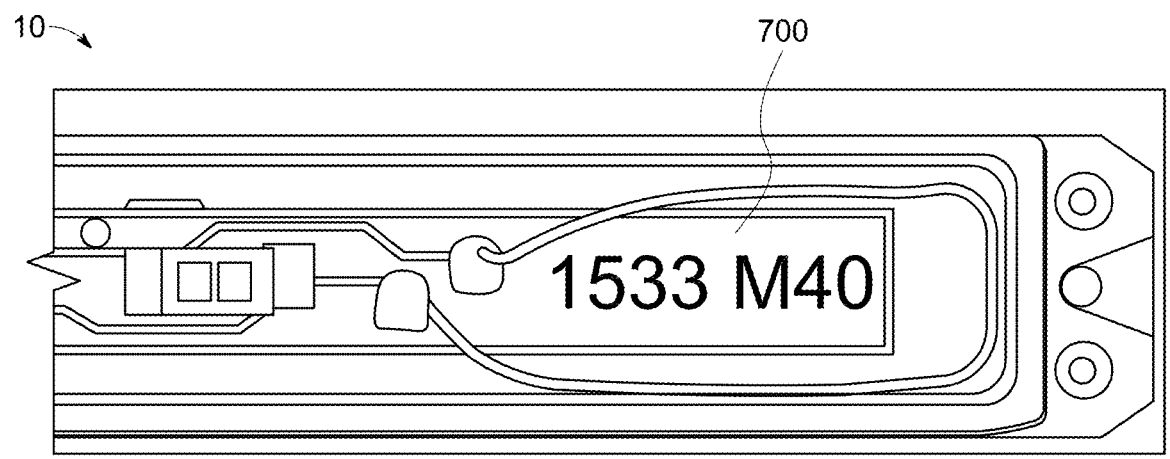
FIG. 28 is a bottom view of a partially assembled implant of the present disclosure, wherein an identification number is visible through the bottom wall.

In another embodiment, the PCB 90 may include indicia 700 printed thereon that may be viewed through the transparent top or bottom walls 60, 50 for identification of the implant 10 as shown in FIG. 28. Additionally, internal components may be inspected for damage or wear. Further, any of a number of visual indicator materials may be inspected: for example, a material in the cavity designed to change color in the presence of humidity would indicate that internal humidity has increased, possibly indicating a breach in the hermetic seal of the housing 20.

It will be further appreciated that although the exemplary embodiments depict a rectangular coil, the coil 30 can be generally circular, ovular, rectangular, or can take the form of any polygon that encloses an area. Additionally, although a rectangular housing is shown in the exemplary embodiment figures, the concept of disposing the walls on the outer periphery of coil 30, parallel to coil axis 35, can be generalized to any polygonal shape. It will be further appreciated that the implant architecture can be used to maximize the size of any internal component, substance, or combination thereof. These may include, but are not limited to, drugs, steroids, batteries, stimulus electrodes, pacing circuitry, flow sensors, chemical sensors, or other electronics.

The disclosed invention may have a further benefit for pressure sensing implants. Many commonly available chip-scale pressure sensors are well suited for use in wireless implants. However, such pressure sensors generally have small, thin, pressure sensing diaphragms, on the order of 2 mm diameter or less and thickness of 500 nm or less. If such a diaphragm is exposed to living tissue or blood, one or more layers of cells will usually grow on it after a period of several days or weeks. Cell layers such as this are known to exhibit a stiffening effect to the sensor's or diaphragm, thereby decreasing the device's sensitivity. In the embodiment, shown in FIGS. 1, 3 and 4, the top wall 60 (and in some embodiments, the bottom wall 50) may serve as flexible pressure diaphragms, which communicate pressure to chip-scale pressure sensors on internal electronics through a pressure-communicating medium. In one embodiment, because the diaphragms of the instant implant are larger in area and generally stiffer than the diaphragms of known chip scale sensors, the top wall 60 will not be stiffened significantly by several layers of cell growth, compared to the smaller diaphragms of the chip-scale sensors. Thus the present invention allows pressure sensor implant designers to select from a number of available off-the-shelf or custom chip-scale pressure sensors, without having to worry about diaphragm stiffening due to cell growth.

The sensor implant housing 20 may be used with RF medical implants, the designs set forth herein are useful for any micro device or component where a non-metal hermetic enclosure is required and where it is desirable to maximize internal cavity space. Examples include, but are not limited to, sensors, actuators, or transponders located in harsh chemical environments, in liquid immersion, in high temperature zones (such as engines), or in environments where sterility is critical. Other examples include applications where the internal electronics must be hermetically housed, but cannot tolerate shielding or eddy current losses imposed by metal housings or braze rings. The designs and methods described herein overcome the many challenges associated with wireless sensors that use radiofrequency.

Figure 16:
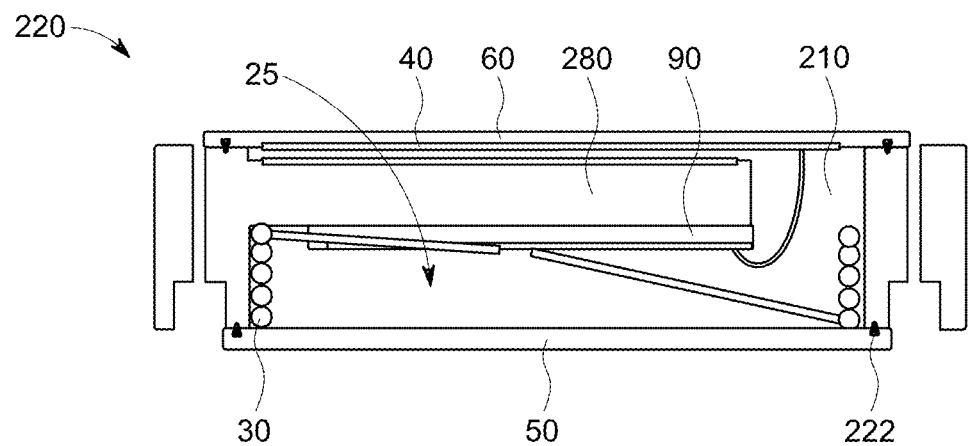
FIG. 16 is a schematic cross-sectional view of an alternate embodiment of the implant of the present disclosure.

There are also numerous variations of the embodiment shown in FIGS. 16-27. For example, as shown in FIG. 16, the housing 220 may be formed from a material having a single continuous construction wherein the top and bottom walls 50, 60 may be attached. The cavity of the housing 220 maybe formed by one of the micromachining processes, chemical etching, conventional machining, or other type of machining known in the art. The cavity 25 may include the coil 30, sensor 40, and other internals inserted into the housing 220. As shown in FIG. 16, housing 220 may be formed with an integral base 280 that is continuous with the side walls of the housing 220 that includes a wirebond cavity 210 to allow attachment between the diaphragm 60 with the PCB 90 and coil 230. The integral base 280 may include a top side and a bottom side wherein the top wall 60 may be adjacent to the top side of the integral base 280 and the bottom wall 50 may be adjacent to the integral base 280. The diaphragm 60 and the bottom wall 50 may be laser welded 222 to the housing 220.

Figure 17:
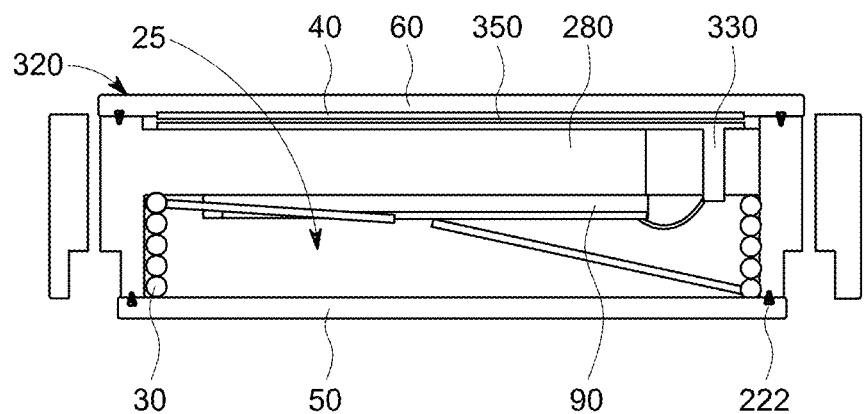
FIG. 17 is a schematic cross-sectional view of an alternate embodiment of the implant of the present disclosure.
Figure 18:
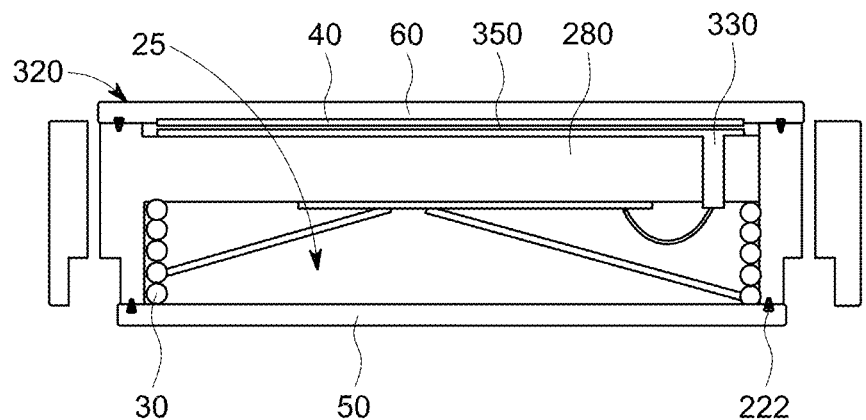
FIG. 18 is a schematic cross-sectional view of an alternate embodiment of the implant of the present disclosure.

FIGS. 17 and 18 depict an embodiment in which the housing 320 may be formed with an integral base 280 that is continuous with the side walls of the housing 220 and includes at least one through substrate via (TSV) 330 to allow attachment between the sensor 40 on the top side of integral base 280 and the PCB 90 (FIG. 17) and coil 30. Alternatively, the sensor 40 may be connected to electronic traces patterned directly on the integral base 280 (FIG. 18). The diaphragm 60 and bottom wall 50 may be laser welded 222 to the housing 320. In these embodiments, use of the TSVs 330 may make the integral base 280 more robust and reduce assembly steps. Also, a capacitive gap 350 may be formed between the integral base 280 and the diaphragm 60. Further, the embodiment of FIG. 18 does not require an attachment between the PCB 90 and base 280 as the electrical traces may be placed directly on the base for attachment to the coil, trimmable capacitors, and wirebonding.

Figure 19:
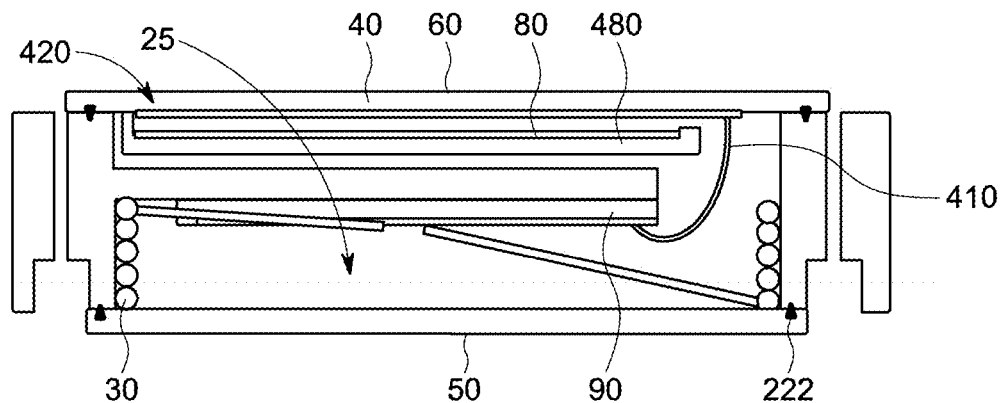
FIG. 19 is a schematic cross-sectional view of an alternate embodiment of the implant of the present disclosure.

In FIG. 19, housing 420 may be made from a continuous material as in FIGS. 16-18 but may include a deep bore for room to receive the sensor 40 as described above. The housing 420 includes a deep shelf 480 to support the PCB 90 thereon and is spaced to allow for attachment in a wirebond cavity 410. Alternatively, deep shelf 480 may be implemented using a separate insert that is fixed to the housing walls by adhesives, press fit, fasteners, or welding. The top and bottom walls 50, 60 are hermetically attached to housing 420 by laser weld 222 as before.

Figure 20:
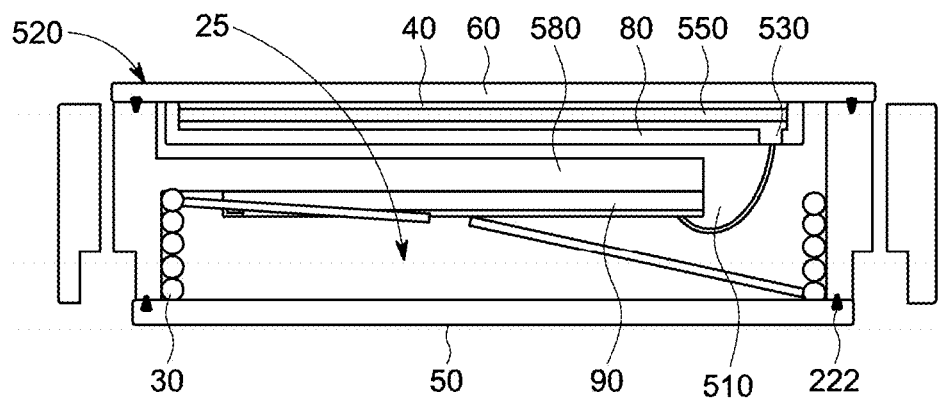
FIG. 20 is a schematic cross-sectional view of an alternate embodiment of the implant of the present disclosure.

In FIG. 20, housing 520 may be made from a continuous material as in FIGS. 16-19 but includes a deep bore for room to receive the sensor 40 as described above. The housing 520 includes a deep shelf 580 to support the PCB 90 thereon and a space to allow for attachment in a wirebond cavity 510. The housing 520 further includes through substrate vias (TSV) 530 to allow attachment between the sensor 40 on the top wall 60 with the PCB 90 and coil 30. The top and bottom walls 50, 60 are hermetically attached to housing 520 by laser weld 222 as before and a hermetic MEMS cavity 550 may be formed between the base 80 and the top wall 60.

Figure 21:
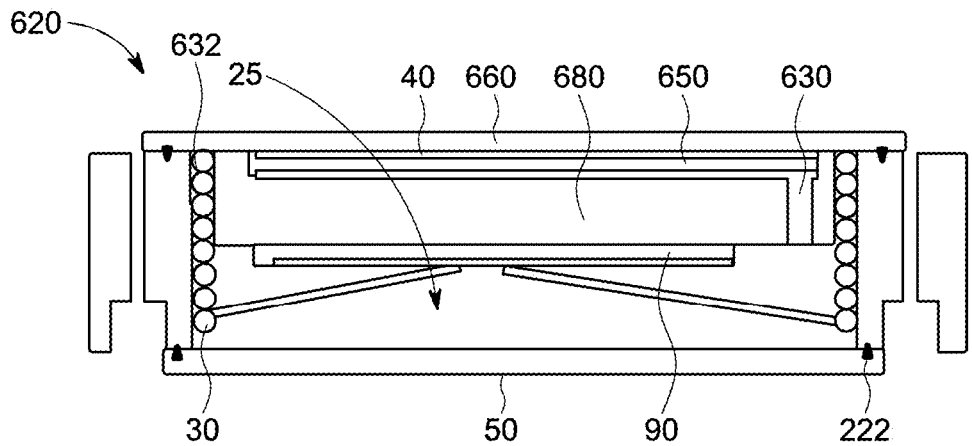
FIG. 21 is a schematic cross-sectional view of an alternate embodiment of the implant of the present disclosure.

In FIG. 21, housing 620 is made from a continuous material as in FIGS. 16-20 but includes a coil cavity 632 to allow room for an enlarged coil 30 and to receive a top wall diaphragm 660 which is part of the sensor 40 with a floating base 680. The coil 30 extends about the base 680. The thick floating base 680 may be attached to the diaphragm 660 and include TSVs 630 as described above. The PCB 90 may be supported on the thick floating base 680 and be attached to TSVs 630 to allow attachment between the sensor 40, the coil 30, and other components. The top and bottom walls 50, 60 are hermetically attached to housing 620 by laser weld 222 as before and a hermetic MEMS cavity 650 may be formed between the base 680 and the diaphragm 660.

The invention disclosed herein is particularly advantageous when the wireless implant is required to be long and narrow, as is typically the case with cardiovascular implants. With such geometries, any coil width gained in the short dimension has a dramatic impact on coil area and hence link distance. In other embodiments, it may be advantageous to use the present invention to increase the height of a coil inside the implant.

Figure 22:
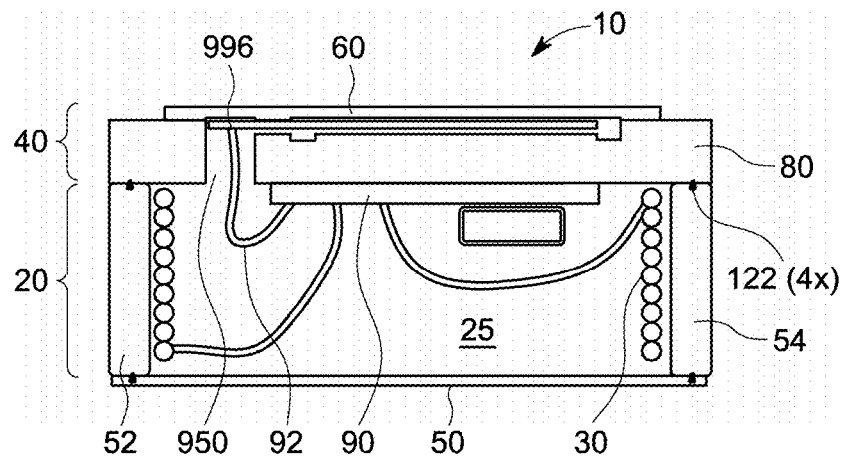
FIG. 22 is a schematic cross-sectional view of an alternate embodiment of the implant of the present disclosure.

FIG. 22 illustrates an alternative embodiment of the implant 10. The sensor 40 may be fabricated as a unit as in previous embodiments, but in this case the base 80 is not "floating" wherein the base 80 may have a perimeter that extends passed portions of the perimeter of the diaphragm 60. The base 80 may include a through hole 950 etched or machined into the base 80 such that bondwires 92 may extend to connect bondpads 996 on the sensor 40 to other bondpads on PCB 90. Other components such as coil 30, PCB 90, and bottom 50 are attached as in previously described embodiments. This alternative embodiment may be somewhat taller overall than embodiments with a floating base, but it may bring about several advantages: (i) the thicker base 80 may make the sensor 40 more robust during handling and other operations during the assembly process; (ii) the weld 122 between the sensor 40 and housing 20 may induce less mechanical stress on the diaphragm 60; (iii) the PCB 90 may induce less stress on the larger base 80, and; (iv) the cavity 25 may have more volume for inclusion of other components described elsewhere.

Figure 23:
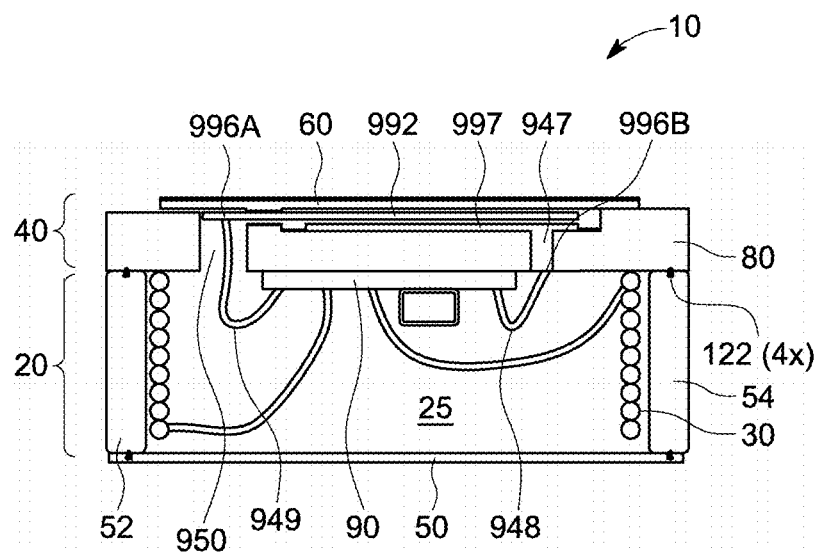
FIG. 23 is a schematic cross-sectional view of an alternate embodiment of the implant of the present disclosure.

FIG. 23 illustrates another alternative embodiment of the implant 10. In this embodiment the sensor 40 is fabricated as a standalone unit as in previous embodiments but in this case the base 80 is not "floating" wherein the base 80 may have a perimeter that extends passed portions of the perimeter of the diaphragm 60. The sensor 40 may be provided with one or more TSVs 947 (described elsewhere) in the base 80, to electrically connect a base electrode 997 to a bondpad 996B located on the bottom side of base 80. The sensor 40 features the large area base 80 and the small area diaphragm 60, as well as the through hole 950 shown in the embodiment of FIG. 22, and resides on top of housing 20. The PCB 90 has bondpads which connect to bondpads 996A and 996B by wirebonds 948 and 949, respectively. Alternatively, the PCB 90 may connect to bondpad 996B using a flipchip connection, such as ball bumping or stud bumping, or any other flipchip technology. This embodiment uses the TSVs 947 to connect directly to the base electrode 997 and the through hole 950 to connect directly to the diaphragm electrode 992. This configuration enables a parallel capacitor arrangement, with one electrode 992 on the diaphragm 60 and one electrode 997 on the base 80. This may be considered a "parallel capacitor" embodiment as distinct from the "serial capacitor" embodiment of FIGS. 2, 3, and 6, which includes two electrodes 48A and 48B along the diaphragm 60 and one electrode 46B along the base 80. The parallel capacitor embodiment may provide twice the capacitance for the same electrode area and gap height as the serial capacitor embodiment which may provide an advantage in performance and design flexibility.

Figure 24:
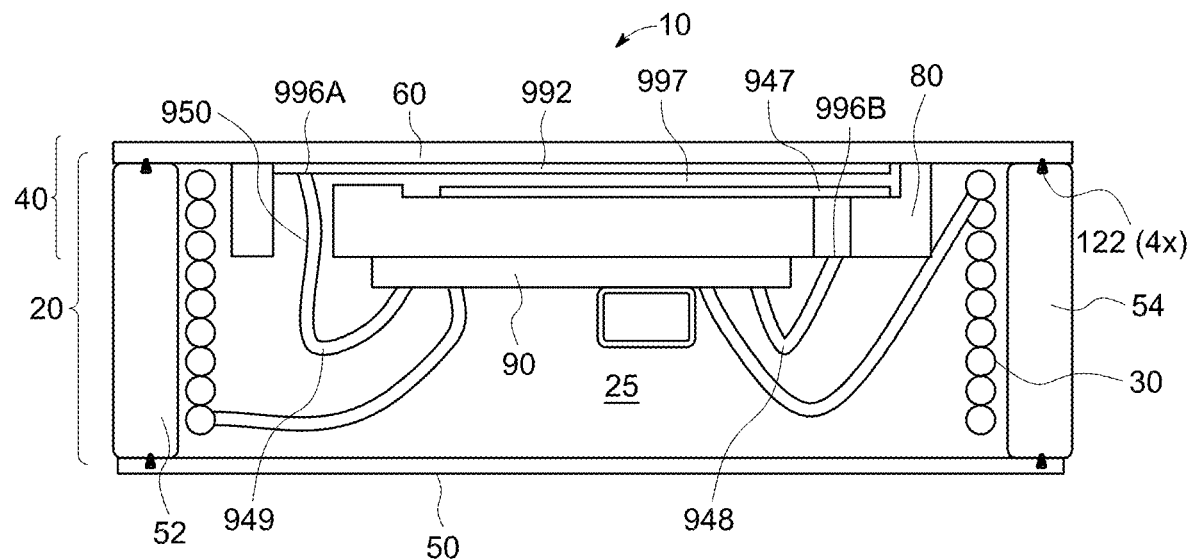
FIG. 24 is a schematic cross-sectional view of an alternate embodiment of the implant of the present disclosure.

FIG. 24 illustrates another alternative embodiment of the implant 10, which combines the concept of the TSV 947 from FIG. 23 with the floating base 80 concept of previous embodiments. Here, the implant 10 may include a parallel capacitor arrangement utilizing TSV 947, as well as the reduced overall height provided by the floating base 80.

Figure 25:
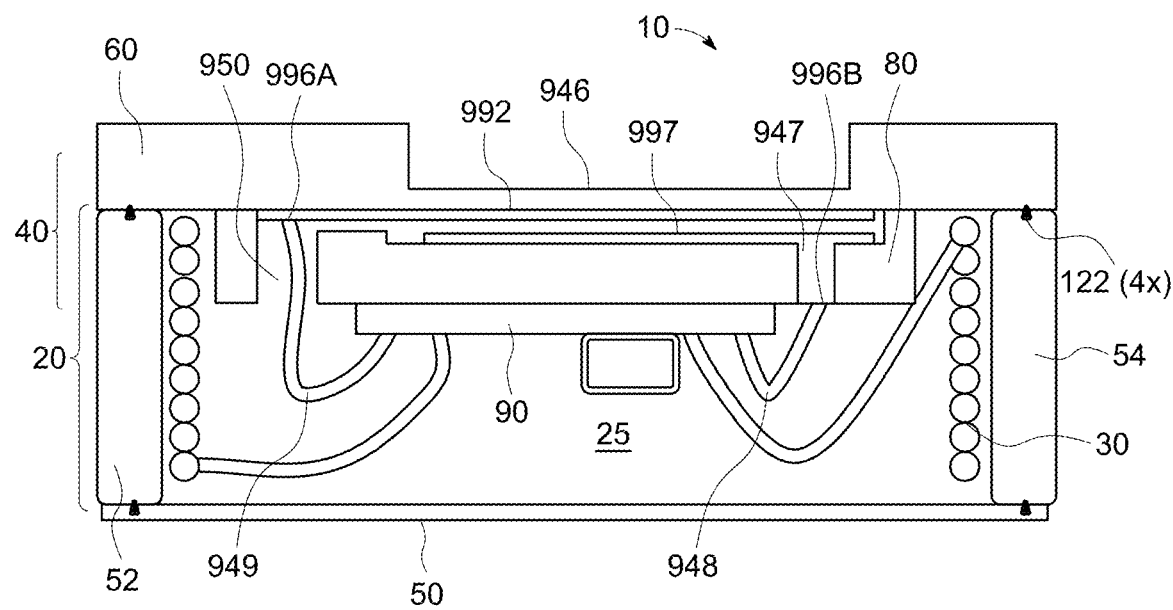
FIG. 25 is a schematic cross-sectional view of an alternate embodiment of the implant of the present disclosure.

FIG. 25 illustrates yet another embodiment of the implant 10. As in FIG. 24, it features TSV 947 and floating base 80. However, the sensor 40 in FIG. 25 has a diaphragm 60 that is, in general, substantially thicker than the diaphragms in other floating base embodiments. The diaphragm 60 may have a thin region 946 machined over an area that is in alignment with the diaphragm electrode 992 and the base electrode 997 of the sensor 40. The thin region 946 may be flexible as the surrounding thicker regions may provide increased mechanical strength that may bring about additional robustness during sensor 40 fabrication, handling, and implant 10 assembly. The increased thickness may also serve to isolate the flexible diaphragm region from stresses on the periphery of diaphragm 60, or from the bond between diaphragm 60 and base 80.

Figure 26:
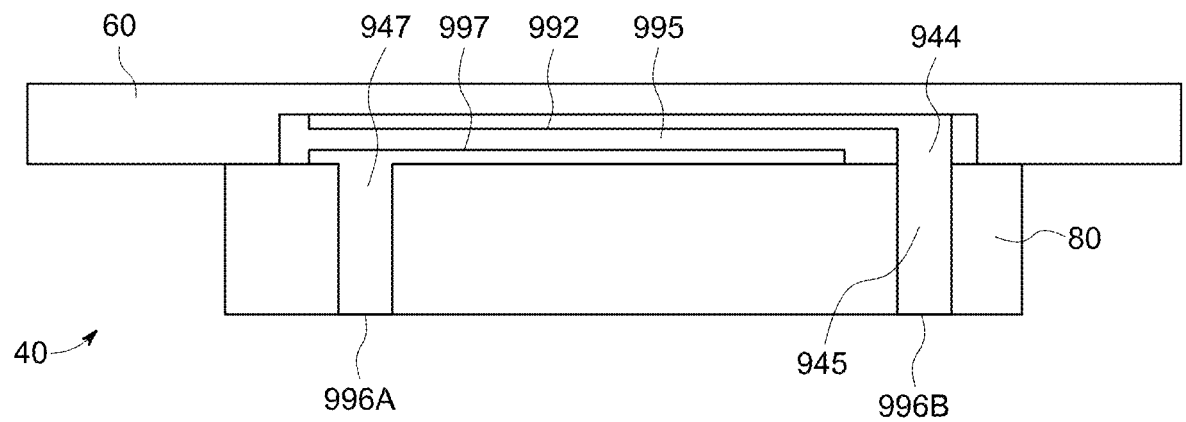
FIG. 26 is a schematic cross-sectional view of an alternate embodiment of the implant of the present disclosure.

FIG. 26 is an alternative embodiment of the sensor 40. As in other embodiments, the base 80 may include one or more TSVs 945, 947 connecting a base electrode 997 to one or more bondpads 996A, 996B on opposite side of the base 80. The base 80 may include one or more TSVs 945, 947 that connect one or more electrodes 992, 997 of the sensor 40 along or adjacent to the diaphragm 60 to one or more pads 996A, 996B on the opposite side of the base 80. A cavity 995 may be formed between the base 80 and the diaphragm 60. The top electrode 992 may electrically connect to the TSV 945 at pad 944 through the cavity 995. The electrical connection may be made by thermo-compression bond, conductive epoxy, eutectic bond, solder reflow, or by capacitive coupling. Note that this multiple TSV concept could also be implemented in a sensor 40 embodiment that has the large base 80 feature as presented in FIG. 22 or 23. In such an embodiment, the through hole 950 and wirebonds 92, 949 in FIGS. 22 and 23 would be replaced by the TSVs 945 and 947 from FIG. 26.

Figure 27:
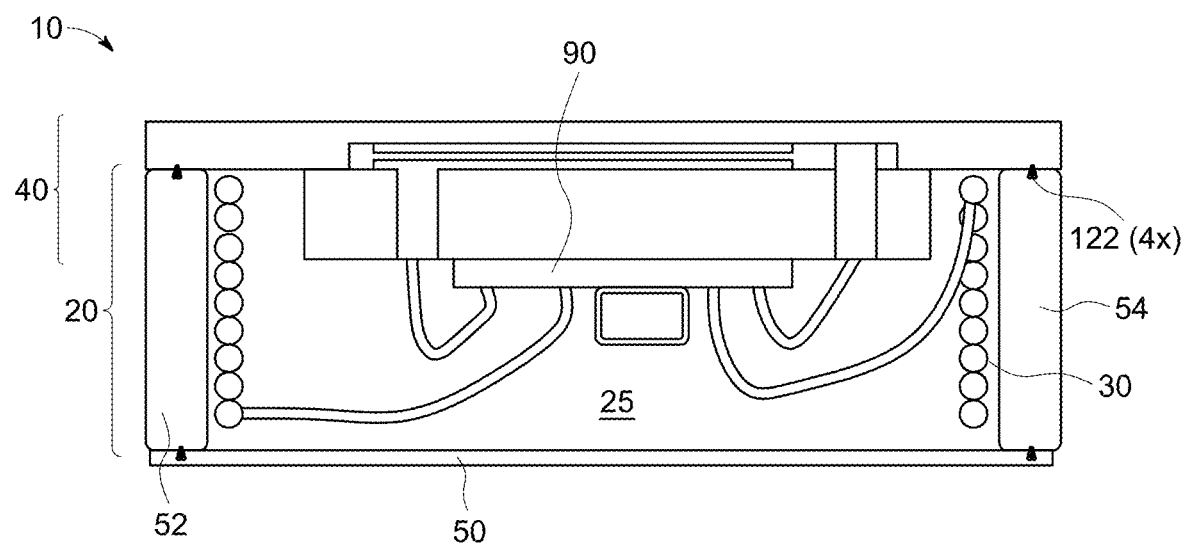
FIG. 27 is a schematic cross-sectional view of an alternate embodiment of the implant of the present disclosure.

FIG. 27 illustrates the sensor 40 embodiment of FIG. 26 incorporated into an implant 10. This embodiment includes PCB 90 from earlier embodiments, but it may also use interconnect patterned directly on the base as described elsewhere.

It can readily be seen that key features from the various embodiments shown in FIGS. 2 and 16 through 27 may be combined together in many other permutations, to achieve different design objectives. The figures are exemplary and intended to illustrate various design features.

Many of the embodiments disclosed herein may benefit from having the final sidewalls attached in a vacuum environment, to prevent internal pressures inside the housing from varying with temperature. Alternatively, the internal volume may be filled with an inert gas to limit corrosion of the internals. This may reduce the risk of problems related to moisture or other particulates.

It will also be appreciated that the implant housing embodiments disclosed herein can be made using all thick walls, and then post-processing the housing to thin portions of the walls that are parallel to the coil's axis. State of the art post-processing technologies such as grinding, polishing, etching, or laser ablation are some possible means for accomplishing this.

In one embodiment, the electrodes may be made of a metal, such as gold. In one embodiment, the TSVs may be made of an electrically conducting material, such as copper, nickel, titanium, or highly doped silicon It will be further appreciated that the embodiments of the invention described herein, as well as housing and wireless implant integration, may be performed at the die level or wafer scale, or some parts at wafer scale and some parts at die level.

The present invention describes several means of manufacturing an implantable wireless pressure sensor. Electronics may be inserted into the housing in a variety of locations and sequences. It should be appreciated that in other embodiments, the wireless sensor may incorporate sensitive biologic, chemical, optical, or other elements to allow for sensing of a variety of metrics.

In all embodiments, the external housing may be surface treated with a biocompatible material to limit clot formation, control cell growth, elute drugs, or improve lubricity. Such materials may include heparin, silicone, parylene, cell tissue monolayers, or other coatings well known to those of ordinary skill in the art. Other materials may be applied or coated onto the housing to improve overall shape for flow dynamics, improved deliverability, or other features. Additional mechanical features may be attached to the housing to facilitate implantation in a desired location in the body. Many such features are disclosed in PCT Patent Application No. PCT/US2011/45583 entitled Pressure Sensor, Centering Anchor, Delivery System and Method, which is also incorporated herein by reference.

While the apparatus and method of subject invention have been shown and described with reference to preferred embodiments, those skilled in the art will readily appreciate that changes and/or modifications may be made thereto without departing from the spirit and scope of the subject invention.

Having thus described the invention, we claim:

1. A wireless implant comprising:
   a housing that defines a cavity;
   a sensor connected to said housing comprising:
      a diaphragm;
      a base positioned entirely within said cavity; and
      at least one adjustable implant component comprising at least one adjustable parameter, wherein said cavity of said housing is hermetically sealed and wherein the at least one adjustable parameter is adjusted by transmitting energy through the housing to inside the cavity to permanently modify at least a part of the at least one adjustable implant component to adjust the at least one adjustable parameter after the housing is hermetically sealed.

2. The implant of claim 1, wherein said base is attached only to said diaphragm.

3. The implant of claim 1, wherein said sensor includes electrical contacts positioned on said diaphragm and wherein said base and diaphragm define a capacitive gap and a vent.

4. The implant of claim 1, wherein said base and said diaphragm define a capacitive gap wherein an attachment between the base and the diaphragm includes a discontinuity configured to connect at least one electrical trace to at least one electrical contact outside of said capacitive gap to at least one electrode positioned at least partially within the capacitive gap.

5. The implant of claim 1, wherein said diaphragm is connected to said housing to form at least part of a hermetic seal about said cavity.

6. The implant of claim 1, wherein the at least one adjustable implant component is a capacitor whose capacitance value may be adjusted by transmitting energy from an outside source through said housing.

7. The implant of claim 1, wherein the at least one adjustable implant component comprises at least one of a capacitor, an electrode, a printed circuit board (PCB), a micro electromechanical systems (MEMS) electrode, a resistor, or an inductor.

8. The implant of claim 1, wherein the at least one adjustable parameter is adjusted by transmitting energy through the housing to inside the cavity to cure the at least one adjustable implant component.

9. The implant of claim 8, wherein the at least one adjustable implant component is an adhesive or coating that is cured via ultraviolet (UV) energy.

10. The implant of claim 1, wherein the at least one adjustable parameter is adjusted by transmitting energy through the housing to inside the cavity to ablate at least a part of the adjustable implant component.

11. The implant of claim 10, wherein the at least one adjustable implant component comprises a capacitor or a track on a printed circuit board (PCB).

12. The implant of claim 1, wherein the at least one adjustable parameter is adjusted by transmitting energy through the housing to inside the cavity to trim at least a part of the adjustable implant component, and wherein the at least one adjustable implant component comprises a micro electromechanical systems (MEMS) electrode, a resistor, or an inductor.

13. The implant of claim 1, wherein the at least one adjustable parameter is adjusted by irradiating gamma particles to inside the cavity, and wherein the gamma particles also function to sterilize the at least one adjustable implant component.

14. The implant of claim 1, wherein the at least one adjustable implant component is permanently modified via at least one of: ultraviolet light, infrared light, focused light, gamma radiation, welding, cutting, soldering, or ablating.

15. A wireless implant comprising:
   a housing that defines a cavity;
   a sensor connected to said housing comprising:
      a diaphragm; and
      a base positioned entirely within said cavity; and
   at least one adjustable implant component comprising at least one adjustable parameter,
   wherein said cavity of said housing is hermetically sealed and wherein the at least one adjustable parameter is adjusted by transmitting energy through the housing to inside the cavity to cure the at least one adjustable implant component to adjust the at least one adjustable parameter after the housing is hermetically sealed.

16. The implant of claim 15, wherein the at least one adjustable implant component is an adhesive or coating that is cured via application of ultraviolet (UV) energy.

17. A wireless implant comprising:
   a housing that defines a cavity;
   a sensor connected to said housing comprising:
      a diaphragm; and
      a base positioned entirely within said cavity; and
   at least one adjustable implant component comprising at least one adjustable parameter,
   wherein said cavity of said housing is hermetically sealed and wherein the at least one adjustable parameter is adjusted by transmitting energy through the housing to inside the cavity to ablate at least a part of the adjustable implant component to adjust the at least one adjustable parameter after the housing is hermetically sealed.

* * * * *